US012317798B2

(12) United States Patent
Iwaki et al.

(10) Patent No.: US 12,317,798 B2
(45) Date of Patent: Jun. 3, 2025

(54) REBAUDIOSIDE M-RICH STEVIA PLANT

(71) Applicant: SUNTORY HOLDINGS LIMITED, Osaka (JP)

(72) Inventors: Kazunari Iwaki, Kanagawa (JP); Katsuro Miyagawa, Kyoto (JP); Tadayoshi Hirai, Kyoto (JP); Naoko Okitsu, Kyoto (JP); Saori Takeyama, Kyoto (JP)

(73) Assignee: SUNTORY HOLDINGS LIMITED, Osaka (JP)

( * ) Notice: Subject to any disclaimer, the term of this patent is extended or adjusted under 35 U.S.C. 154(b) by 48 days.

(21) Appl. No.: 16/754,621

(22) PCT Filed: Oct. 12, 2018

(86) PCT No.: PCT/JP2018/038064
§ 371 (c)(1),
(2) Date: Apr. 8, 2020

(87) PCT Pub. No.: WO2019/074089
PCT Pub. Date: Apr. 18, 2019

(65) Prior Publication Data
US 2020/0281141 A1    Sep. 10, 2020

(30) Foreign Application Priority Data
Oct. 12, 2017   (JP) ................. 2017-198515

(51) Int. Cl.
| *A01H 6/14* | (2018.01) |
| *A01H 5/06* | (2018.01) |
| *A01H 5/10* | (2018.01) |
| *A01H 5/12* | (2018.01) |
| *A23L 2/60* | (2006.01) |
| *A23L 27/30* | (2016.01) |
| *A23L 33/105* | (2016.01) |
| *A61K 47/46* | (2006.01) |
| *C12N 5/04* | (2006.01) |
| *C12Q 1/683* | (2018.01) |
| *C12Q 1/686* | (2018.01) |
| *C12Q 1/6895* | (2018.01) |

(52) U.S. Cl.
CPC .......... *A01H 6/1488* (2018.05); *A01H 5/06* (2013.01); *A01H 5/10* (2013.01); *A01H 5/12* (2013.01); *A23L 2/60* (2013.01); *A23L 27/36* (2016.08); *A23L 33/105* (2016.08); *A61K 47/46* (2013.01); *C12N 5/04* (2013.01); *C12Q 1/683* (2013.01); *C12Q 1/686* (2013.01); *C12Q 1/6895* (2013.01); *A23V 2002/00* (2013.01); *C12Q 2600/13* (2013.01); *C12Q 2600/156* (2013.01)

(58) Field of Classification Search
CPC ................................... A01H 6/1488
See application file for complete search history.

(56) References Cited

U.S. PATENT DOCUMENTS

| 2016/0057955 A1 | 3/2016 | Li et al. |
| 2017/0226145 A1* | 8/2017 | Zhang ............. A23L 27/36 |
| 2017/0283819 A1 | 10/2017 | Markosyan et al. |

FOREIGN PATENT DOCUMENTS

| JP | 2009-517043 | 4/2009 |
| JP | 2016-515814 | 6/2016 |
| WO | 2007/070224 | 6/2007 |
| WO | 2014/146084 | 9/2014 |
| WO | WO 2016/049531 | * 3/2016 |
| WO | 2017/171023 | 10/2017 |

OTHER PUBLICATIONS

GLG develops stevia leaf seedling with 1000% increase of rebaudioside M, Nutraceutical Business Review, Mar. 1, 2016.*
Yadav et al., 2011, A review on the improvement of stevia (*Stevia rebaudiana* Bertoni), Can J. Plant Sci. 91: 1-27.*
Madan et al., 2010, Stevia rebaudiana (Bert). Bertoni—A Review, Indian Journal of Natural Products and Resources 1: 267-286.*
Shyn et al Journal of Agricultural Research China vol. 43, No. 1, pp. 29-39 includes Summary in English (Year: 1994).*
GLG Life Tech Corporation Announces Major Developments in High Reb M Stevia Plants and Product Innovations Press Release of Sep. 21, 2017 (Year: 2017).*
International Search Report issued in PCT/JP2018/038064, mailed Dec. 25, 2018, along with an English-language translation.
Written Opinion of the International Search Authority issued in PCT/JP2018/038064, mailed Dec. 25, 2018, along with an English-language translation.
Extended European Search Report issued in EP Patent Application No. 18866807.3, dated Jun. 22, 2021.
"Novel Stevia Varieties with Superior Taste Profile for Sweeteners", msut.technologypublisher.com/technology/22776, contact: T. Herlache, published Sep. 2, 2016.
Prakash et al., "Development of Next Generation Stevia Sweetener: Rebaudioside M." *Foods*, vol. 3, No. 1, pp. 162-175, 2014.

* cited by examiner

*Primary Examiner* — David H Kruse
(74) *Attorney, Agent, or Firm* — GREENBLUM & BERNSTEIN, P.L.C.

(57) ABSTRACT

The present invention provides a high rebaudioside M content non-genetically modified *stevia* plant comprising rebaudioside M at higher content as compared with the wild type *stevia* species. The present invention also provides a method of producing such a high rebaudioside M content non-genetically modified *stevia* plant, and a dry leaf obtainable from such a plant.

7 Claims, 2 Drawing Sheets

Specification includes a Sequence Listing.

REBAUDIOSIDE M-RICH STEVIA PLANT

TECHNICAL FIELD

The present invention relates to a *stevia* plant with high content of rebaudioside M.

BACKGROUND ART

In response to consumers' diversified needs, various drinks have been developed and are commercially available. Saccharides such as sucrose are components very commonly blended in drinks for the purpose of, for example, conferring sweetness. However, their influence on health due to excessive consumption has been pointed out. Thus, there are growing needs for lower calorie and naturally derived sweeteners. For example, Patent Literature 1 discloses a functional sweetener composition containing a vitamin, a high intensity sweetener, and a sweetness improving composition.

Rebaudioside (hereinafter, also referred to as "Reb") is known as a sweet component contained in a *stevia* extract. The *stevia* extract is obtained by extraction and purification from a *stevia* leaf. Stevia is a perennial plant of the family Asteraceae with Paraguay in the South America as its place of origin, and its scientific name is *Stevia rebaudiana* Bertoni. Stevia contains a component having approximately 300 or more times the sweetness of sugar and is therefore cultivated for use of this sweet component extracted therefrom as a natural sweetener. The presence of various glycosides such as RebA, RebB, RebC, RebD, RebE and RebM has been reported as Reb (JP 2012-504552 A). Among various Rebs, for example, RebA is evaluated as a high intensity sweetener having good quality of sweetness and is widely used. The other Rebs have also been increasingly found to have their unique sweetness and associated taste.

Under these circumstances, a *stevia* plant containing 0.38% by weight of rebaudioside M and 3.28% by weight of rebaudioside D per dry leaf is known (Patent Literature 3).

CITATION LIST

Patent Literature

[Patent Literature 1] JP 2009-517043 A
[Patent Literature 2] National Publication of International Patent Application No. 2016-515814
[Patent Literature 3] US2016/0057955A1

DISCLOSURE OF THE INVENTION

Problems to be Solved by the Invention

Rebaudioside M reportedly has good quality of taste, among steviol glycosides, but cannot be obtained in large amounts from natural *stevia* plants. Thus, the obtainment thereof is of concern.

Means for Solving the Problems

The present invention provides a high rebaudioside M content non-genetically modified *stevia* plant containing rebaudioside M at high content as compared with the wild type *stevia* species, a method of producing the plant, and a method of screening for the plant.

Specifically, the present invention provides the following.

[1-1]
A high rebaudioside M content non-genetically modified *stevia* plant comprising 2% or more of rebaudioside M with respect to the amount of total steviol glycoside contained in a leaf.

[1-2]
The plant according to [1-1], further comprising 9.5% or more of rebaudioside D with respect to the amount of total steviol glycoside contained in a leaf.

[1-3]
The plant according to [1-1] or [1-2] having at least one of the following genetic features (1) to (5).
  (1) Homozygous for the allele wherein the base at the position corresponding to position 44 of SEQ ID NO:35 is T.
  (2) Homozygous for the allele wherein the base at the position corresponding to position 40 of SEQ ID NO:37 is T.
  (3) Homozygous for the allele wherein the base at the position corresponding to position 48 of SEQ ID NO:39 is C.
  (4) Homozygous for the allele wherein the portion corresponding to positions 55-72 of SEQ ID NO:42 is deleted.
  (5) Homozygous for the allele wherein the base at the position corresponding to position 50 of SEQ ID NO:43 is A.

[1-4]
The plant according to any one of [1-1] to [1-3], wherein the plant is positive for at least one polymorphic marker selected from the group consisting of P01 to P05.

[1-5]
A seed, a tissue, a tissue culture or a cultured plant cell of the plant according to any one of [1-1] to [1-4].

[1-6]
The tissue, tissue culture or the cultured plant cell according to [1-5], which is an embryo, a meristem cell, a pollen, a leaf, a root, a root apex, a petal, a protoplast, a leaf section or a callus.

[1-7]
A method of producing a high rebaudioside M content *stevia* plant comprising 2% or more of rebaudioside M with respect to the amount of total steviol glycoside contained in a leaf, the method comprising a step of crossing a *stevia* plant according to any one of [1-1] to [1-4] with a second *stevia* plant.

[1-8]
The method according to [1-7], wherein the second plant is the *stevia* plant according to any one of [1-1] to [1-4].

[1-9]
An extract of the plant according to any one of [1-1] to [1-4], the seed, tissue, tissue culture or cell according to [1-5].

[1-10]
A food or drink product, a sweetener composition, a flavor or a medicament comprising the extract according to [1-9].

[1-11]
A method of producing a rebaudioside M-containing extract, comprising a step of obtaining an extract from the plant according to any one of [1-1] to [1-4], the seed, tissue, tissue culture or cell according to [1-5].

[1-12]
A method of producing rebaudioside M, comprising a step of purifying rebaudioside M from a rebaudioside M-containing extract according to [1-11].

[1-13]
A method of producing a food or drink product, a sweetener composition, a flavor or a medicament, comprising a step of mixing an extract obtained by the method according to [1-11] and/or rebaudioside M obtained by the method according to [1-12] with other components.

[1-14]

A method of screening for a high rebaudioside M content stevia plant, comprising a step of detecting the presence and/or the absence of at least one of the following genetic features (1) to (5) from the genome of a test plant.
  (1) Homozygous for the allele wherein the base at the position corresponding to position 44 of SEQ ID NO:35 is T.
  (2) Homozygous for the allele wherein the base at the position corresponding to position 40 of SEQ ID NO:37 is T.
  (3) Homozygous for the allele wherein the base at the position corresponding to position 48 of SEQ ID NO:39 is C.
  (4) Homozygous for the allele wherein the portion corresponding to positions 55-72 of SEQ ID NO:42 is deleted.
  (5) Homozygous for the allele wherein the base at the position corresponding to position 50 of SEQ ID NO:43 is A.

[1-15]

The method according to [1-14], comprising a step of detecting at least one polymorphic marker selected from the group consisting of P01 to P05 from the genome of a test plant.

[1-16]

The method according to [1-14] or [1-15], further comprising a step of measuring the content of rebaudioside M in a leaf tissue.

[1-17]

Any one or more primer set(s) selected from the group consisting of:
  (1) a primer set comprising a forward primer having or comprising a sequence of any 15 or more consecutive bases in SEQ ID NO: 1 and a reverse primer having or comprising a sequence of any 15 or more consecutive bases in SEQ ID NO: 2;
  (2) a primer set comprising a forward primer having or comprising a sequence of any 15 or more consecutive bases in SEQ ID NO: 3 and a reverse primer having or comprising a sequence of any 15 or more consecutive bases in SEQ ID NO: 4;
  (3) a primer set comprising a forward primer having or comprising a sequence of any 15 or more consecutive bases in SEQ ID NO: 5 and a reverse primer having or comprising a sequence of any 15 or more consecutive bases in SEQ ID NO: 6;
  (4) a primer set comprising a forward primer having or comprising a sequence of any 15 or more consecutive bases in SEQ ID NO: 7 and a reverse primer having or comprising a sequence of any 15 or more consecutive bases in SEQ ID NO: 8; and
  (5) a primer set comprising a forward primer having or comprising a sequence of any 15 or more consecutive bases in SEQ ID NO: 9 and a reverse primer having or comprising a sequence of any 15 or more consecutive bases in SEQ ID NO: 10, wherein the sequence of any 15 or more consecutive bases is positioned at the 3' end of each primer.

[1-18]

A kit comprising a primer set according to [1-17] and optionally a restriction enzyme, wherein in case the primer set comprises a forward primer having or comprising a sequence of any contiguous 15 bases or more in SEQ ID NO: 1, the restriction enzyme comprises XbaI;

in case the primer set comprises a forward primer having or comprising a sequence of any consecutive 15 bases or more in SEQ ID NO:3, the restriction enzyme comprises KpnI;

in case the primer set comprises a forward primer having or comprising a sequence of any consecutive 15 bases or more in SEQ ID NO:5, the restriction enzyme comprises AflII; and in case the primer set comprises a forward primer having or comprising a sequence of any consecutive 15 bases or more in SEQ ID NO: 9, the restriction enzyme comprises PvuI.

[1-19]

A probe comprising a nucleotide sequence shown in any one of SEQ ID NOs: 55 to 64, the probe being optionally bound with a detectable label.

[1-20]

The probe according to [1-19], wherein the probe has a fluorescent label, a dye or a binding moiety.

[1-21]

A method of screening for a high rebaudioside M content non-genetically modified stevia plant, comprising steps of: performing PCR amplification using a primer set according to [1-17] on genomic DNA of a test plant for the purpose of detecting at least one polymorphic marker selected from the group consisting of P01 to P05; and, when the polymorphic marker is at least one member selected from the group consisting of P01 to P03 and P05, treating a PCR product obtained by the PCR amplification with a restriction enzyme, and detecting a restriction enzyme-treated product.

[1-22]

The method according to [1-21], wherein the restriction enzyme is at least one member selected from the group consisting of XbaI, KpnI, AflII and PvuI.

[1-23]

The method according to [1-21], wherein the polymorphic marker comprises P02 and P05.

[1-24]

The method according to [1-23], wherein the restriction enzyme comprises KpnI and PvuI.

[1-25]

The method according to any one of [1-21] to [1-24], wherein the plant obtained by the screening comprises 2% or more of rebaudioside M with respect to the amount of total steviol glycoside contained in a leaf.

The present invention also provides the following.

[2-1]

A high rebaudioside M content non-genetically modified stevia plant comprising 2% or more of rebaudioside M with respect to the amount of total steviol glycoside contained in a dry leaf.

[2-2]

The plant according to [2-1], further comprising 9.5% or more of rebaudioside D with respect to the amount of total steviol glycoside contained in a dry leaf.

[2-3]

The plant according to [2-1] or [2-2], wherein the plant is positive for at least one polymorphic marker selected from the group consisting of P01, P02, P03, P04 and P05.

[2-4]
A seed of the plant according to any one of [2-1] to [2-3].
[2-5]
A dry leaf of the plant according to any one of [2-1] to [2-3].
[2-6]
A tissue culture or a cultured plant cell of a plant according to any one of [2-1] to [2-3].
[2-7]
The tissue culture or the cultured plant cell according to [2-6], wherein the tissue culture or the cultured plant cell is an embryo, a meristem cell, a pollen, a leaf, a root, a root apex, a petal, a protoplast, a leaf section or a callus.
[2-8]
A method of producing a high rebaudioside M content *stevia* plant comprising 2% or more of rebaudioside M with respect to the amount of total steviol glycoside contained in a dry leaf, the method comprising a step of crossing a *stevia* plant according to any one of [2-1] to [2-3] with a second *stevia* plant.
[2-9]
The method according to [2-8], wherein the second plant is the *stevia* plant according to any one of [2-1] to [2-3].
[2-10]
An extract of the plant according to any one of [2-1] to [2-3], the seed according to [2-4] or the dry leaf according to [2-5].
[2-11]
A food or drink product, a sweetener composition, a flavor or a medicament comprising the extract according to [2-10].
[2-12]
A method of producing a rebaudioside M-containing extract, comprising a step of obtaining an extract from the plant according to any one of [2-1] to [2-3], the seed according to [2-4] or the dry leaf according to [2-5].
[2-13]
A method of producing rebaudioside M, comprising a step of purifying rebaudioside M from a rebaudioside M-containing extract according to [2-12].
[2-14]
A method of producing a food or drink product, a sweetener composition, a flavor or a medicament, comprising a step of mixing an extract obtained by the method according to [2-12] and/or rebaudioside M obtained by the method according to [2-13] with other components.
[2-15]
A method of screening for a high rebaudioside M content *stevia* plant, comprising a step of detecting at least one polymorphic marker selected from the group consisting of P01, P02, P03, P04 and P05 from the genome of a test plant.
[2-16]
The method according to [2-15], further comprising a step of measuring the content of rebaudioside M in a leaf tissue.
[2-17]
Any one or more primer set(s) selected from the group consisting of:
(1) a primer set comprising a forward primer having or comprising a sequence of any 15 or more consecutive bases in SEQ ID NO: 1 and a reverse primer having or comprising a sequence of any 15 or more consecutive bases in SEQ ID NO: 2;
(2) a primer set comprising a forward primer having or comprising a sequence of any 15 or more consecutive bases in SEQ ID NO: 3 and a reverse primer having or comprising a sequence of any 15 or more consecutive bases in SEQ ID NO: 4;
(3) a primer set comprising a forward primer having or comprising a sequence of any 15 or more consecutive bases in SEQ ID NO: 5 and a reverse primer having or comprising a sequence of any 15 or more consecutive bases in SEQ ID NO: 6;
(4) a primer set comprising a forward primer having or comprising a sequence of any 15 or more consecutive bases in SEQ ID NO: 7 and a reverse primer having or comprising a sequence of any 15 or more consecutive bases in SEQ ID NO: 8; and
(5) a primer set comprising a forward primer having or comprising a sequence of any 15 or more consecutive bases in SEQ ID NO: 9 and a reverse primer having or comprising a sequence of any 15 or more consecutive bases in SEQ ID NO: 10, wherein
the sequence of any 15 or more consecutive bases is positioned at the 3' end of each primer.
[2-18]
A kit comprising at least one primer set selected from the primer sets (1) to (5) according to [2-17] and a restriction enzyme, wherein
the restriction enzyme is XbaI for the primer set (1),
the restriction enzyme is KpnI for the primer set (2),
the restriction enzyme is AflII for the primer set (3), and
the restriction enzyme is PvuI for the primer set (5).
[2-19]
A probe comprising a nucleotide sequence shown in any one of SEQ ID NOs: 1 to 10, the probe being optionally bound with a detectable label.
[2-20]
The probe according to [2-19], wherein the probe has a fluorescent label, a dye or a binding moiety.
[2-21]
A method of screening for a high rebaudioside M content non-genetically modified *stevia* plant, comprising steps of: performing PCR amplification using a primer set according to [2-17] on genomic DNA of a test plant for the purpose of detecting at least one polymorphic marker selected from the group consisting of P01, P02, P03, P04 and P05; and, when the polymorphic marker is at least one member selected from the group consisting of P01, P02, P03 and P05, treating a PCR product obtained by the PCR amplification with a restriction enzyme, and detecting a restriction enzyme treated product.
[2-22]
The method according to [2-21], wherein the restriction enzyme is at least one member selected from the group consisting of XbaI, KpnI, AflII and PvuI.
[2-23]
The method according to [2-21], wherein the polymorphic marker is P02 and P05.
[2-24]
The method according to [2-23], wherein the restriction enzyme is KpnI and PvuI.
[2-25]
The method according to any one of [2-21] to [2-24], wherein the plant obtained by the screening comprises 2% or more of rebaudioside M with respect to the amount of total steviol glycoside contained in a dry leaf.

Advantageous Effects of Invention

The present invention enables the obtainment of a *stevia* plant richer in rebaudioside M and the provision of an approach for producing such a plant, a leaf obtainable from such a plant, and a food, a drink, etc. containing rebaudioside M obtained from this leaf.

DESCRIPTION OF EMBODIMENTS

Figure 1:
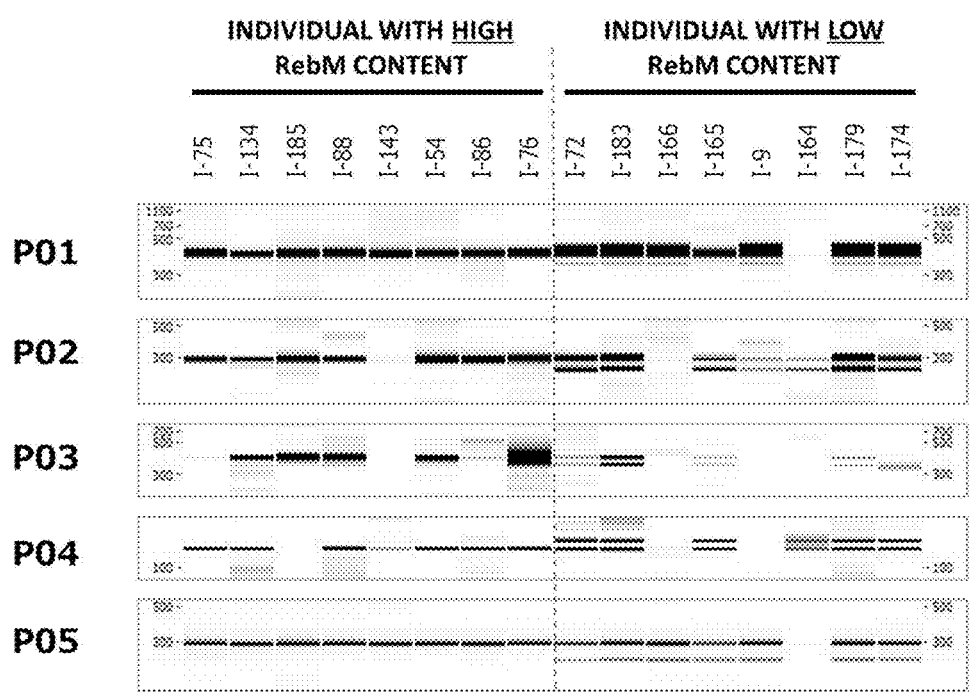
FIG. 1 shows electrophoresis images obtained in the marker detection of individual group I.

Hereinafter, the present invention will be described in detail. The embodiments are given below merely for illustrating the present invention and are not intended to limit the present invention by such embodiments. The present invention can be carried out in various modes without departing from the spirit of the present invention.

Note that all documents, as well as laid-open application publications, patent application publications, and other patent documents cited herein shall be incorporated herein by reference. The present specification incorporates the contents of the specification and the drawings of Japanese Patent Application No. 2017-198515, filed on Oct. 12, 2017, from which the present application claims priority.

1. High Rebaudioside M Content Non-Genetically Modified *Stevia* Plant of the Present Invention The present invention provides a high rebaudioside M content non-genetically modified *stevia* plant comprising 2% or more of rebaudioside M with respect to the amount of total steviol glycoside contained in a leaf (e.g., dry leaf or fresh leaf) (hereinafter, referred to as the "plant of the present invention" or "*stevia* plant of the present invention").

The *stevia* plant of the present invention is a species derived from a *stevia* plant of wild species, but a gene variation which increases the level of rebaudioside M has occurred. The gene variation occurs in a non-genetically modified manner (mentioned later).

In the present invention, among high rebaudioside M content non-genetically modified *stevia* plants, a *stevia* plant comprising 2 to 4.6% of rebaudioside M with respect to the amount of total steviol glycoside contained in a leaf (e.g., dry leaf or fresh leaf) may also be referred to as a high rebaudioside M content non-genetically modified *stevia* plant, and a *stevia* plant comprising 4.7% or more of rebaudioside M with respect thereto may also be referred to as an ultra-high rebaudioside M content non-genetically modified *stevia* plant.

The total steviol glycoside (TSG) neither includes an unknown steviol glycoside nor includes a steviol glycoside present at a level less than the detection limit. Preferably, the total steviol glycoside is any combination of two or more members selected from the group consisting of rebaudioside A, rebaudioside B, rebaudioside M, rebaudioside D, rebaudioside E, rebaudioside F, rebaudioside I, rebaudioside J, rebaudioside K, rebaudioside N, rebaudioside M, rebaudioside O, rebaudioside Q, rebaudioside R, dulcoside A, rubusoside, steviol, steviolmonoside, steviolbioside and stevioside. In a certain embodiment, the total steviol glycoside may consist of, for example, rebaudioside A, rebaudioside B, rebaudioside M, rebaudioside D, rebaudioside F, rebaudioside M and steviol. In another embodiment, the total steviol glycoside may consist of rebaudioside A, rebaudioside B, rebaudioside M, rebaudioside D, rebaudioside F, rebaudioside M, rebaudioside N, rebaudioside O and steviol.

[Formula 1]

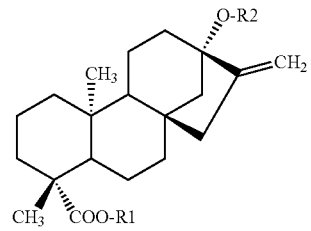

| Compound name | R1 | R2 |
|---|---|---|
| 1 Steviol | H | H |
| 2 Steviolbioside | H | β-Glc-β-Glc(2→1) |
| 3 Stevioside | β-Glc | β-Glc-β-Glc(2→1) |
| 4 Rebaudioside A | β-Glc | β-Glc-β-Glc(2→1)<br>\|<br>β-Glc(3→1) |
| 5 Rebaudioside B | H | β-Glc-β-Glc(2→1)<br>\|<br>β-Glc(3→1) |
| 6 Rebaudioside C | β-Glc | β-Glc-α-Rha(2→1)<br>\|<br>β-Glc(3→1) |
| 7 Rebaudioside D | β-Glc-β-Glc(2→1) | β-Glc-β-Glc(2→1)<br>\|<br>β-Glc(3→1) |
| 8 Rebaudioside E | β-Glc-β-Glc(2→1) | β-Glc-β-Glc(2→1) |
| 9 Rebaudioside F | β-Glc | β-Glc-β-Xyl(2→1)<br>\|<br>β-Glc(3→1) |
| 10 Rubusoside | β-Glc | β-Glc |
| 11 Dulcoside A | β-Glc | β-Glc-α-Rha(2→1) |
| 12 Rebaudioside M | β-Glc-β-Glc(2→1)<br>\\<br>β-Glc(3→1) | β-Glc-β-Glc(2→1)<br>\\<br>β-Glc(3→1) |
| 14 Rebaudioside N | β-Glc-α-Rha(2→1)<br>\\<br>β-Glc(3→1) | β-Glc-β-Glc(2→1)<br>\\<br>β-Glc(3→1) |

The feature "comprising 2% or more of rebaudioside M with respect to the amount of total steviol glycoside contained in a leaf (e.g., dry leaf or fresh leaf)" is characterized in that, when the content of rebaudioside M (RebM) is indicated by RebM/TSG % as the ratio to the total amount of steviol glycosides obtained from a leaf, the lower limit of the value of RebM/TSG is 2% or more, 3% or more, 4% or more, 5% or more, 6% or more, 7% or more, 8% or more, 9% or more, 10% or more, 12% or more, 14% or more, 16% or more, 18% or more, 20% or more, 22% or more, 24% or more, 26% or more, 28% or more, 30% or more, 32% or more, 34% or more, 36% or more, or 38% or more. On the other hand, the above feature is characterized in that the upper limit of the value of RebM/TSG is 15% or less, 16% or less, 18% or less, 20% or less, 22% or less, 24% or less, 26% or less, 28% or less, 30% or less, 32% or less, 34% or less, 36% or less, 38% or less, or 40% or less. The combination of the lower limit and the upper limit is not particularly limited as long as the upper limit value is larger than the lower limit value in the combination. One having this ratio of 2% or more and less than 4.7% may be referred to as a high rebaudioside M content phenotype, and one having this ratio of 4.7% or more and 15% or less may be referred to as an ultra-high rebaudioside M content phenotype.

The plant of the present invention may also comprise 0.19 g or more of rebaudioside M in 100 g of a dry leaf. This means that, when a dry leaf is obtained from the plant of the present invention, rebaudioside M is present in an amount of 0.19 g or more, 0.20 g or more, 0.25 g or more, 0.30 g or more, 0.35 g or more, 0.40 g or more, 0.45 g or more, 0.50 g or more, 0.55 g or more, 0.60 g or more, 0.65 g or more, 0.70 g or more, 0.75 g or more, 0.80 g or more, 0.85 g or more, 0.90 g or more, 0.95 g or more, 1.00 g or more, 1.05 g or more, 1.10 g or more, 1.15 g or more, 1.20 g or more, 1.25 g or more, 1.30 g or more, 1.35 g or more, 1.40 g or more, or 1.45 g or more per 100 g of the dry leaf.

In this context, the dry leaf of the plant of the present invention refers to a leaf having a water content decreased to 3 to 4% by weight by drying a fresh leaf of the *stevia* plant of the present invention.

In this context, the plant of the present invention may further comprise 1.00 g or more, 1.05 g or more, 1.10 g or more, 1.15 g or more, 1.20 g or more, 1.25 g or more, 1.30 g or more, 1.35 g or more, 1.40 g or more, 1.45 g or more, 1.50 g or more, 1.55 g or more, 1.60 g or more, 1.65 g or more, 1.70 g or more, 1.75 g or more, 1.80 g or more, 1.85 g or more, 1.90 g or more, 1.95 g or more, 2.00 g or more, 2.05 g or more, 2.10 g or more, 2.15 g or more, 2.20 g or more, 2.25 g or more, 2.30 g or more, 2.35 g or more, 2.40 g or more, 2.45 g or more, 2.50 g or more, 2.55 g or more, 2.60 g or more, 2.65 g or more, 2.70 g or more, 2.75 g or more, 2.80 g or more, 2.85 g or more, 2.90 g or more, 2.95 g or more, 3.00 g or more, 3.05 g or more, 3.10 g or more, 3.15 g or more, 3.20 g or more, 3.25 g or more, 3.30 g or more, 3.35 g or more, 3.40 g or more, 3.45 g or more, 3.50 g or more, 3.55 g or more or 3.57 g or more of rebaudioside D in 100 g of a dry leaf.

In this context, the combination of the rebaudioside M and D contents is not particularly limited and includes any combination.

Preferably, the plant of the present invention comprises 1.03 g or more of rebaudioside M and 1.1 g or more of rebaudioside D in 100 g of a dry leaf.

Alternatively, the leaf (e.g., dry leaf or fresh leaf) of the plant of the present invention, when the amount (g) of rebaudioside M contained per 100 g of a leaf of the wild type *stevia* plant is defined as 100%, may comprise rebaudioside M at higher content by 300% or more, 400% or more, 500% or more, 600% or more, 700% or more, 800% or more, 900% or more, 1100% or more, 1200% or more, 1300% or more, 1400% or more, 1500% or more, 1600% or more, 1700% or more, 1800% or more, 1900% or more, 2000% or more, 2100% or more, 2200% or more, 2300% or more, 2400% or more, 2500% or more, 2600% or more, 2700% or more, 2800% or more, 2900% or more, or 3000% or more as compared with the wild type *stevia* species.

The *stevia* plant of the present invention is characterized in that, when the content of rebaudioside M (RebM) and rebaudioside D (RebD) in a leaf (e.g., dry leaf or fresh leaf) is indicated by RebM/RebD ratio, the lower limit of the value of RebM/RebD is 0.2 or more, 0.3 or more, 0.4 or more, 0.5 or more, 0.6 or more, 0.8 or more, or 1.0 or more. On the other hand, it is characterized in that the upper limit of the value of RebM/RebD is 0.3 or less, 0.4 or less, 0.5 or less, 0.6 or less, 0.8 or less, 1.0 or less, 1.1 or less, or 1.2 or less. The combination of the lower limit and the upper limit is not particularly limited as long as the upper limit value is larger than the lower limit value in the combination. The ratio is preferably 0.2 or more and 1.2 or less, or 0.6 or more and 1.1 or less.

The *stevia* plant of the present invention is characterized in that, when the content of rebaudioside M (RebM) and rebaudioside D (RebD) in a leaf (e.g., dry leaf or fresh leaf) is indicated by (RebD+RebM)/TSG % as the ratio to the total amount of steviol glycosides, the lower limit of the value of (RebD+RebM)/TSG is 14% or more, 16% or more, 18% or more, 20% or more, 22% or more, 24% or more, 26% or more, 28% or more, 30% or more, 32% or more, 34% or more, 36% or more, or 38% or more. On the other hand, it is characterized in that the upper limit of the value of (RebD+RebM)/TSG is 18% or less, 20% or less, 22% or less, 24% or less, 26% or less, 28% or less, 30% or less, 32% or less, 34% or less, 36% or less, 38% or less, or 40% or less. The combination of the lower limit and the upper limit is not particularly limited as long as the upper limit value is larger than the lower limit value in the combination. The ratio is preferably 14% or more and 40% or less, or 16% or more and 40% or less.

In an alternative embodiment, the plant of the present invention may have a total amount of steviol glycosides smaller than that of the wild type. Specifically, the plant of the present invention may comprise less than 19 g as the total amount of steviol glycosides in 100 g of a dry leaf. This means that when a dry leaf is obtained from the plant of the present invention, the total amount of steviol glycosides is less than 19 g, less than 18 g, less than 17 g, less than 16 g, less than 15 g, less than 14 g, less than 13 g, less than 12 g, less than 11 g, less than 10 g, less than 9 g, less than 8 g, or less than 7 g per 100 g of the dry leaf.

The *stevia* plant of the present invention is characterized in that, when the content of rebaudioside M (RebM) and rebaudioside A (RebA) in 100 g of a leaf (e.g., dry leaf or fresh leaf) is indicated by RebM/RebA ratio, the lower limit of the value of RebM/RebA is 0.03 or more, 0.04 or more, 0.05 or more, 0.06 or more, 0.08 or more, 0.10 or more, 0.12 or more, or 0.14 or more. On the other hand, it is characterized in that the upper limit of the value of RebM/RebA is 0.08 or less, 0.10 or less, 0.12 or less, 0.14 or less, 0.16 or less, 0.18 or less, 0.20 or less, 0.24 or less, or 0.26 or less. The combination of the lower limit and the upper limit is not particularly limited as long as the upper limit value is larger than the lower limit value in the combination. The ratio is preferably 0.03 or more and 0.26 or less, or 0.10 or more and 0.26 or less.

The *stevia* plant of the present invention is characterized in that, when the content of rebaudioside M (RebM) and rebaudioside A (RebA) in 100 g of a leaf (e.g., dry leaf or fresh leaf) is indicated by (RebA+RebM)/TSG as the ratio to the total amount of steviol glycosides, the lower limit of the value of (RebA+RebM)/TSG is 4% or more, 5% or more, 6% or more, 7% or more, 8% or more, 9% or more, 10% or more, 12% or more, 14% or more, 16% or more, 18% or more, 20% or more, 22% or more, 24% or more, 26% or more, 28% or more, 30% or more, 32% or more, 34% or more, 36% or more, or 38% or more. On the other hand, it is characterized in that the upper limit of the value of (RebA+RebM)/TSG is 10% or less, 12% or less, 14% or less, 16% or less, 18% or less, 20% or less, 22% or less, 24% or less, 26% or less, 28% or less, 30% or less, 32% or less, 34% or less, 36% or less, 38% or less, or 40% or less. The combination of the lower limit and the upper limit is not particularly limited as long as the upper limit value is larger than the lower limit value in the combination. The ratio is preferably 4% or more and 40% or less, or 16% or more and 40% or less.

As mentioned above, the *stevia* plant of the present invention has a variation involved in the increase of the level of rebaudioside M. Such variation has at least one of the following genetic features (1) to (5) (hereinafter, may be referred to as the "genetic feature(s) of the present invention").

(1) Homozygous for the allele wherein the base at the position corresponding to position 44 of SEQ ID NO:35 is T.
(2) Homozygous for the allele wherein the base at the position corresponding to position 40 of SEQ ID NO:37 is T.
(3) Homozygous for the allele wherein the base at the position corresponding to position 48 of SEQ ID NO:39 is C.
(4) Homozygous for the allele wherein the portion corresponding to positions 55-72 of SEQ ID NO:42 is deleted.
(5) Homozygous for the allele wherein the base at the position corresponding to position 50 of SEQ ID NO:43 is A.

The phrase "position (or portion) corresponding to" means the following. In case a sequence identical to a reference sequence (e.g., SEQ ID NOs: 35, 37, 39, 42, 43, etc.) is present in the genome, it means a position or a portion in the sequence (e.g., 44, 40, 48, 55-72, 50, etc.) present in the genome, and in case a sequence identical to the reference sequence is not present in the genome, it means a position or portion in a sequence in the genome corresponding to the reference sequence, which corresponds to the position or portion in the reference sequence. Whether or not a sequence identical to or corresponding to the reference sequence exists in the genome can be determined by, for example, amplifying genomic DNA of the *stevia* plant of interest with a primer capable of amplifying the reference sequence by PCR, sequencing the amplified product, and performing alignment analysis between the obtained sequence and the reference sequence. Non-limiting examples of a sequence corresponding to a reference sequence include, for example, a base sequence having a sequence identity of 60% or more, 70% or more, 75% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 98.1% or more, 98.4% or more, 98.7% or more, 99.2% or more, 99.5% or more, or 99.8% or more to the reference sequence. The position or portion corresponding to the position or portion in the reference sequence in the sequence corresponding to the reference sequence in the genome can be determined by taking into account the base sequence before and after the position or portion in the reference sequence and the like. For example, a position or portion in the sequence corresponding to the reference sequence in the genome corresponding to a position or portion in the reference sequence can be determined by an alignment analysis of a reference sequence with a sequence corresponding to a reference sequence in the genome.

For instance, when taking "the position corresponding to position 44 of SEQ ID NO:35" of the genetic feature (1) as an example, in case the genome of a *stevia* plant has a portion consisting of a base sequence identical to SEQ ID NO:35, "the position corresponding to position 44 of SEQ ID NO:35" is position 44 from the 5'-end of the portion consisting of a base sequence identical to SEQ ID NO:35 in the genome. On the other hand, in case the genome of a *stevia* plant has a portion consisting of a base sequence which is not identical to, but which corresponds to SEQ ID NO:35, the genome does not have a portion consisting of a base sequence identical to SEQ ID NO:35. Therefore, "the position corresponding to position 44 of SEQ ID NO:35" does not necessarily correspond to position 44 from the 5'-end of the portion corresponding to SEQ ID NO:35. However, it is possible to identify "the position corresponding to position 44 of SEQ ID NO:35" in the genome of such a *stevia* plant by taking into account the base sequence before and after the position 44 of SEQ ID NO:35, and the like. For instance, one can identify "the position corresponding to position 44 of SEQ ID NO:35" in the genome of a *stevia* plant by an alignment analysis of the base sequence of a portion corresponding to SEQ ID NO:35" in the genome of a *stevia* plant and the base sequence of SEQ ID NO:35.

"The portion consisting of a base sequence corresponding to SEQ ID NO:35" means, for instance, a portion consisting of a base sequence having a sequence identity of 60% or more, 70% or more, 75% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 98.1% or more, 98.4% or more, 98.7% or more, 99% or more, 99.2% or more, 99.5% or more, or 99.8% or more to the base sequence of SEQ ID NO:35.

In one embodiment, "the portion consisting of a base sequence corresponding to SEQ ID NO:35" includes a portion of the genome of a *stevia* plant which can be amplified by PCR using a forward primer which hybridizes to a complementary sequence of a portion of 15 to 25 base long from the 5'-end of SEQ ID NO:35 and a reverse primer which hybridizes to a portion of 15 to 25 base long from the 3'-end of SEQ ID NO:35

For simplicity, the genetic feature (1) is used here as an example for explanation, but the same applies to the genetic features (2) to (5).

In a specific embodiment, "the portion consisting of a base sequence corresponding to SEQ ID NO:35" includes, for instance, a portion of the genome of a *stevia* plant which can be amplified by PCR using a forward primer comprising the base sequence of SEQ ID NO:45 and a reverse primer comprising the base sequence of SEQ ID NO:46.

In a specific embodiment, "the portion consisting of a base sequence corresponding to SEQ ID NO:37" includes, for instance, a portion of the genome of a *stevia* plant which can be amplified by PCR using a forward primer comprising the base sequence of SEQ ID NO:47 and a reverse primer comprising the base sequence of SEQ ID NO:48.

In a specific embodiment, "the portion consisting of a base sequence corresponding to SEQ ID NO:39" includes, for instance, a portion of the genome of a *stevia* plant which can be amplified by PCR using a forward primer comprising the base sequence of SEQ ID NO:49 and a reverse primer comprising the base sequence of SEQ ID NO:50.

In a specific embodiment, "the portion consisting of a base sequence corresponding to SEQ ID NO:42" includes, for instance, a portion of the genome of a *stevia* plant which can be amplified by PCR using a forward primer comprising the base sequence of SEQ ID NO:51 and a reverse primer comprising the base sequence of SEQ ID NO:52.

In a specific embodiment, "the portion consisting of a base sequence corresponding to SEQ ID NO:43" includes, for instance, a portion of the genome of a *stevia* plant which can be amplified by PCR using a forward primer comprising the base sequence of SEQ ID NO:53 and a reverse primer comprising the base sequence of SEQ ID NO:54.

In a specific embodiment, "the allele wherein the base at the position corresponding to position 44 of SEQ ID NO: 35 is T" comprises the base sequence of SEQ ID NO: 55, 65 or 75.

In a specific embodiment, "the allele wherein the base at the position corresponding to position 40 of SEQ ID NO: 37 is T" comprises the base sequence of SEQ ID NO: 57, 67 or 77.

In a specific embodiment, "the allele wherein the base at the position corresponding to position 48 of SEQ ID NO: 39 is C" comprises the base sequence of SEQ ID NO: 59, 69 or 79.

In a specific embodiment, "the allele wherein the portion corresponding to positions 55-72 of SEQ ID NO:42 is deleted" comprises the base sequence of SEQ ID NO: 61, 71 or 81.

In a specific embodiment, "the allele wherein the base at the position corresponding to position 50 of SEQ ID NO: 43 is A" comprises the base sequence of SEQ ID NO: 63, 73 or 83.

Here, a position selected from the group consisting of (1) a position corresponding to position 44 of SEQ ID NO: 35, (2) a position corresponding to position 40 of SEQ ID NO: 37, (3) a position corresponding to position 48 of SEQ ID NO: 39, (4) a portion corresponding to positions 55-72 of SEQ ID NO: 42, and (5) a position corresponding to position 50 of SEQ ID NO: 43 may be referred to as a "polymorphic site of the present invention" or a "variation site of the present invention".

Also, a variation selected from the group consisting of (1) a variation from A to T at a position corresponding to position 44 of SEQ ID NO: 35, (2) a variation from C to T at a position corresponding to position 40 of SEQ ID NO: 37, (3) a variation from G to C at a position corresponding to position 48 of SEQ ID NO: 39, (4) a deletion of the portion corresponding to positions 55-72 of SEQ ID NO: 42, and (5) a variation from G to A at a position corresponding to position 50 of SEQ ID NO: 43 may be referred to as a "polymorphism of the present invention" or a "variation of the present invention".

The above genetic features can be detected by PCR method, TaqMan PCR method, sequencing method, microarray method, Invader method, TILLING method, RAD (random amplified polymorphic DNA) method, restriction fragment length polymorphism (RFLP) method, PCR-SSCP method, AFLP (amplified fragment length polymorphism) method, SSLP (simple sequence length polymorphism) method, CAPS (cleaved amplified polymorphic sequence) method, dCAPS (derived cleaved amplified polymorphic sequence) method, allele-specific oligonucleotide (ASO) method, ARMS method, denaturing gradient gel electrophoresis (DGGE) method, CCM (chemical cleavage of mismatch) method, DOL method, MALDI-TOF/MS method, TDI method, padlock probe method, molecular beacon method, DASH (dynamic allele specific hybridization) method, UCAN method, ECA method, PINPOINT method, PROBE (primer oligo base extension) method, VSET (very short extension) method, Survivor assay, Sniper assay, Luminex assay, GOOD method, LCx method, SNaP-shot method, Mass ARRAY method, pyrosequencing method, SNP-IT method, melting curve analysis method, etc., but detection methods are not limited thereto.

In a specific embodiment, the above genetic features are detectable on the basis of "polymorphic marker positivity" using a polymorphic marker developed by the present inventors.

In this context, the polymorphic marker is at least one member selected from the group consisting of P01 to P05.

The positivity for P01 means that only a band of approximately 383 bp long (e.g., SEQ ID NO: 21) is obtained by: performing PCR amplification using a forward primer having the nucleotide sequence shown in SEQ ID NO: 1 and a reverse primer having the nucleotide sequence shown in SEQ ID NO: 2 on the genomic DNA of a candidate plant; and treating the obtained PCR product (approximately 383 bp long: e.g., SEQ ID NO: 21 or 22) with an XbaI restriction enzyme. On the other hand, when a restriction enzyme-treated product of approximately 344 bp (e.g., SEQ ID NO: 23) is formed by the XbaI restriction enzyme treatment of the PCR product, the candidate plant is negative for P01.

The positivity for P02 means that only a band of approximately 297 bp long (e.g., SEQ ID NO: 24) is obtained by: performing PCR amplification using a forward primer having the nucleotide sequence shown in SEQ ID NO: 3 and a reverse primer having the nucleotide sequence shown in SEQ ID NO: 4 on the genomic DNA of a candidate plant; and treating the obtained PCR product (297 bp long) (e.g., SEQ ID NO: 24 or 25) with a KpnI restriction enzyme. On the other hand, when a restriction enzyme-treated product of approximately 258 bp (e.g., SEQ ID NO: 26) is formed, the candidate plant is negative for P02.

The positivity for P03 means that only a band of approximately 390 bp long (e.g., SEQ ID NO: 27) is obtained by: performing PCR amplification using a forward primer having the nucleotide sequence shown in SEQ ID NO: 5 and a reverse primer having the nucleotide sequence shown in SEQ ID NO: 6 on the genomic DNA of a candidate plant; and treating the obtained PCR product (approximately 390 bp long) (e.g., SEQ ID NO: 27 or 28) with an AflII restriction enzyme. On the other hand, when a restriction enzyme-treated product of approximately 347 bp (e.g., SEQ ID NO: 29) is formed, the candidate plant is negative for P03.

The positivity for P04 means that only a PCR product of approximately 140 bp (e.g., SEQ ID NO: 30) is formed by performing PCR amplification using a forward primer having the nucleotide sequence shown in SEQ ID NO: 7 and a reverse primer having the nucleotide sequence shown in SEQ ID NO: 8 on the genomic DNA of a candidate plant. When PCR products of 140 bp (e.g., SEQ ID NO: 30) and 158 bp (e.g., SEQ ID NO: 34) are formed, the candidate plant is negative for thereto.

The positivity for P05 means that only a band of approximately 288 bp long (e.g., SEQ ID NO: 31) is obtained by: performing PCR amplification using a forward primer having the nucleotide sequence shown in SEQ ID NO: 9 and a reverse primer having the nucleotide sequence shown in SEQ ID NO: 10 on the genomic DNA of a candidate plant; and treating the obtained PCR product (approximately 288 bp long) (e.g., SEQ ID NO: 31 or 32) with a PvuI restriction enzyme. On the other hand, when a restriction enzyme-treated product of approximately 240 bp (e.g., SEQ ID NO: 33) is formed, the candidate plant is negative for P05.

The term "approximately" as to bp long described above means±5 bp. The restriction enzyme treatment can be performed according to conditions recommended by the distributor of each restriction enzyme used.

For the detailed method of screening for the plant of the present invention, see the section "3. Method of screening for plant of present invention" mentioned later.

The above genetic features (e.g., polymorphism positive for the above-mentioned polymorphic marker has been confirmed in Examples to have statistical correlation with high rebaudioside M content and/or highly rebaudioside D-containing phenotypes.

The rebaudioside M or D can be extracted in the state of a liquid extract by reacting a fresh leaf or a dry leaf of the plant of the present invention with a suitable solvent (an aqueous solvent such as water or an organic solvent such as an alcohol, ether or acetone). For the extraction conditions, etc., see a method described in Ohta et al., J. Appl. Glycosci., Vol. 57, No. 3 (2010) or WO2010/038911, or a method described in Examples mentioned later.

The rebaudioside M can be further purified from the liquid extract thus obtained by use of a method known in the art such as a gradient of ethyl acetate or any of other organic solvents:water, high performance liquid chromatography (HPLC), gas chromatography, time-of-flight mass spectrometry (TOF-MS), or ultra (high) performance liquid chromatography (UPLC).

The rebaudioside M content according to the present invention can be measured by a method described in Ohta et al., J. Appl. Glycosci., Vol. 57, No. 3 (2010) or WO2010/038911, or a method described in Examples mentioned later. Specifically, a fresh leaf can be sampled from the *stevia* plant of the present invention, followed by measurement by LC/MS-MS.

The plant of the present invention may include not only the whole plant but a plant organ (e.g., a leaf, a petal, a stem, a root, and a seed), a plant tissue (e.g., epidermis, phloem, soft tissue, xylem, vascular bundle, palisade tissue, and spongy tissue), various forms of plant cells (e.g., suspended cultured cells), a protoplast, a leaf section, a callus, and the like. The leaf may be the dry leaf mentioned above.

The plant of the present invention may also include a tissue culture or a cultured plant cell. This is because the plant can be regenerated by culturing such a tissue culture or a cultured plant cell. Examples of the tissue culture or the cultured plant cell of the plant of the present invention include, but are not limited to, embryos, meristem cells, pollens, leaves, roots, root apices, petals, protoplasts, leaf sections and calluses.

2. Method of Producing Plant of Present Invention

In an alternative aspect, the present invention provides a method of producing a high rebaudioside M content *stevia* plant comprising 2% or more of rebaudioside M with respect to the amount of total steviol glycoside contained in a leaf (e.g., dry leaf or fresh leaf), the method comprising a step of crossing the *stevia* plant of the present invention with a second *stevia* plant (hereinafter, may be referred to as the "production method of the present invention").

The "high rebaudioside M content *stevia* plant comprising 2% or more of rebaudioside M with respect to the amount of total steviol glycoside contained in a leaf" produced by the method has the same phenotype and genetic properties as those of the plant of the present invention.

Specifically, when a leaf (e.g., dry leaf or fresh leaf) is obtained from the plant obtained by the production method of the present invention, the leaf comprises 2% or more of rebaudioside M with respect to the amount of total steviol glycoside contained in the leaf. This is characterized in that, when the content of rebaudioside M (RebM) is indicated by RebM/TSG % as the ratio to the total amount of steviol glycosides obtained from the dry leaf, the lower limit of the value of RebM/TSG is 2% or more, 3% or more, 4% or more, 5% or more, 6% or more, 7% or more, 8% or more, 9% or more, 10% or more, 12% or more, 14% or more, 16% or more, 18% or more, 20% or more, 22% or more, 24% or more, 26% or more, 28% or more, 30% or more, 32% or more, 34% or more, 36% or more, or 38% or more. On the other hand, this means that the upper limit of the value of RebM/TSG is 15% or less, 16% or less, 18% or less, 20% or less, 22% or less, 24% or less, 26% or less, 28% or less, 30% or less, 32% or less, 34% or less, 36% or less, 38% or less, or 40% or less. The combination of the lower limit and the upper limit is not particularly limited as long as the upper limit value is larger than the lower limit value in the combination. The ratio is preferably 2% or more and 20% or less, or 7% or more and 15% or less.

The plant obtained by the production method of the present invention may also comprise 0.19 g or more of rebaudioside M in 100 g of a dry leaf. This means that, when a dry leaf is obtained from the plant of the present invention, rebaudioside M is present in an amount of 0.19 g or more, 0.20 g or more, 0.25 g or more, 0.30 g or more, 0.35 g or more, 0.40 g or more, 0.45 g or more, 0.50 g or more, 0.55 g or more, 0.60 g or more, 0.65 g or more, 0.70 g or more, 0.75 g or more, 0.80 g or more, 0.85 g or more, 0.90 g or more, 0.95 g or more, 1.00 g or more, 1.05 g or more, 1.10 g or more, 1.15 g or more, 1.20 g or more, 1.25 g or more, 1.30 g or more, 1.35 g or more, 1.40 g or more, or 1.45 g or more per 100 g of the dry leaf.

In this context, the plant obtained by the production method of the present invention may further comprise 1.00 g or more, 1.05 g or more, 1.10 g or more, 1.15 g or more, 1.20 g or more, 1.25 g or more, 1.30 g or more, 1.35 g or more, 1.40 g or more, 1.45 g or more, 1.50 g or more, 1.55 g or more, 1.60 g or more, 1.65 g or more, 1.70 g or more, 1.75 g or more, 1.80 g or more, 1.85 g or more, 1.90 g or more, 1.95 g or more, 2.00 g or more, 2.05 g or more, 2.10 g or more, 2.15 g or more, 2.20 g or more, 2.25 g or more, 2.30 g or more, 2.35 g or more, 2.40 g or more, 2.45 g or more, 2.50 g or more, 2.55 g or more, 2.60 g or more, 2.65 g or more, 2.70 g or more, 2.75 g or more, 2.80 g or more, 2.85 g or more, 2.90 g or more, 2.95 g or more, 3.00 g or more, 3.05 g or more, 3.10 g or more, 3.15 g or more, 3.20 g or more, 3.25 g or more, 3.30 g or more, 3.35 g or more, 3.40 g or more, 3.45 g or more, 3.50 g or more, 3.55 g or more or 3.57 g or more of rebaudioside D in 100 g of a dry leaf.

In this context, the combination of the rebaudioside M and D contents is not particularly limited and includes any combination.

Preferably, the plant obtained by the production method of the present invention comprises 1.03 g or more of rebaudioside M and 1.1 g or more of rebaudioside D in 100 g of a dry leaf.

Alternatively, when the amount (g) of rebaudioside M contained per 100 g of a leaf (e.g., dry leaf or fresh leaf) of the wild type *stevia* plant is defined as 100%, the leaf of the plant obtained by the production method of the present invention may comprise rebaudioside M at higher content by 300% or more, 400% or more, 500% or more, 600% or more, 700% or more, 800% or more, 900% or more, 1100% or more, 1200% or more, 1300% or more, 1400% or more, 1500% or more, 1600% or more, 1700% or more, 1800% or more, 1900% or more, 2000% or more, 2100% or more, 2200% or more, 2300% or more, 2400% or more, 2500% or more, 2600% or more, 2700% or more, 2800% or more, 2900% or more, or 3000% or more as compared with the wild type *stevia* species.

The plant obtained by the production method of the present invention is characterized in that, when the content of rebaudioside M (RebM) and rebaudioside D (RebD) in a leaf (e.g., dry leaf or fresh leaf) is indicated by RebM/RebD ratio, the lower limit of the value of RebM/RebD is 0.2 or more, 0.3 or more, 0.4 or more, 0.5 or more, 0.6 or more, 0.8 or more, or 1.0 or more. On the other hand, it is characterized in that the upper limit of the value of RebM/RebD is 0.3 or less, 0.4 or less, 0.5 or less, 0.6 or less, 0.8 or less, 1.0 or less, 1.1 or less, or 1.2 or less. The combination of the lower limit and the upper limit is not particularly limited as long as the upper limit value is larger than the lower limit value in the combination. The ratio is preferably 0.2 or more and 1.2 or less, or 0.6 or more and 1.1 or less.

The plant obtained by the production method of the present invention is characterized in that, when the content of rebaudioside M (RebM) and rebaudioside D (RebD) in a leaf (e.g., dry leaf or fresh leaf) is indicated by (RebD+RebM)/TSG % as the ratio to the total amount of steviol glycosides, the lower limit of the value of (RebD+RebM)/TSG is 14% or more, 16% or more, 18% or more, 20% or more, 22% or more, 24% or more, 26% or more, 28% or more, 30% or more, 32% or more, 34% or more, 36% or more, or 38% or more. On the other hand, it is characterized in that the upper limit of the value of (RebD+RebM)/TSG is 18% or less, 20% or less, 22% or less, 24% or less, 26% or less, 28% or less, 30% or less, 32% or less, 34% or less, 36% or less, 38% or less, or 40% or less. The combination of the lower limit and the upper limit is not particularly limited as long as the upper limit value is larger than the lower limit value in the combination. The ratio is preferably 14% or more and 40% or less, or 16% or more and 40% or less.

In an alternative embodiment, the plant obtained by the production method of the present invention may have a total amount of steviol glycosides smaller than that of the wild type. Specifically, the plant obtained by the production method of the present invention may comprise less than 19 g as the total amount of steviol glycosides in 100 g of a dry leaf. This means that, when a dry leaf is obtained from the plant of the present invention, the total amount of steviol glycosides per 100 g of the dry leaf is less than 19 g, less than 18 g, less than 17 g, less than 16 g, less than 15 g, less than 14 g, less than 13 g, less than 12 g, less than 11 g, less than 10 g, less than 9 g, less than 8 g, or less than 7 g.

The plant obtained by the production method of the present invention is characterized in that, when the content of rebaudioside M (RebM) and rebaudioside A (RebA) in 100 g of a leaf (e.g., dry leaf or fresh leaf) is indicated by the (RebA+RebM)/TSG as the ratio to the total amount of steviol glycosides, the lower limit of the value of (RebA+RebM)/TSG is 4% or more, 5% or more, 6% or more, 7% or more, 8% or more, 9% or more, 10% or more, 12% or more, 14% or more, 16% or more, 18% or more, 20% or more, 22% or more, 24% or more, 26% or more, 28% or more, 30% or more, 32% or more, 34% or more, 36% or more, 38% or more, or 40% or more. On the other hand, it is characterized in that the upper limit of the value of (RebA+RebM)/TSG is 30% or less, 32% or less, 34% or less, 36% or less, 38% or less, 40% or less, 42% or less, 44% or less, 46% or less, 48% or less, 50% or less, 52% or less, 54% or less, 56% or less, 58% or less, 60% or less, 62% or less, 64% or less, 66% or less, 68% or less, 70% or less, 72% or less, 74% or less, 76% or less, 78% or less, or 80% or less. The combination of the lower limit and the upper limit is not particularly limited as long as the upper limit value is larger than the lower limit value in the combination. The ratio is preferably 4% or more and 80% or less, or 40% or more and 80% or less.

The plant obtained by the production method of the present invention has at least one of the following genetic features (1) to (5) involved in the increase of the level of rebaudioside M.

(1) Homozygous for the allele wherein the base at the position corresponding to position 44 of SEQ ID NO:35 is T.
(2) Homozygous for the allele wherein the base at the position corresponding to position 40 of SEQ ID NO:37 is T.
(3) Homozygous for the allele wherein the base at the position corresponding to position 48 of SEQ ID NO:39 is C.
(4) Homozygous for the allele wherein the portion corresponding to positions 55-72 of SEQ ID NO:42 is deleted.
(5) Homozygous for the allele wherein the base at the position corresponding to position 50 of SEQ ID NO:43 is A.

Such genetic features are detectable as being "polymorphic marker positive" using a polymorphic marker developed by the present inventors.

In this context, the polymorphic marker is at least one member selected from the group consisting of P01 to P05.

The positivity for P01 means that only a band of approximately 383 bp long (e.g., SEQ ID NO: 21) is obtained by: performing PCR amplification using a forward primer having the nucleotide sequence shown in SEQ ID NO: 1 and a reverse primer having the nucleotide sequence shown in SEQ ID NO: 2 on the genomic DNA of a candidate plant; and treating the obtained PCR product (approximately 383 bp long: e.g., SEQ ID NO: 21 or 22) with an XbaI restriction enzyme. On the other hand, when a restriction enzyme-treated product of approximately 344 bp (e.g., SEQ ID NO: 23) is formed by the XbaI restriction enzyme treatment of the PCR product, the candidate plant is negative for P01.

The positivity for P02 means that only a band of approximately 297 bp long (e.g., SEQ ID NO: 24) is obtained by: performing PCR amplification using a forward primer having the nucleotide sequence shown in SEQ ID NO: 3 and a reverse primer having the nucleotide sequence shown in SEQ ID NO: 4 on the genomic DNA of a candidate plant; and treating the obtained PCR product (297 bp long) (e.g., SEQ ID NO: 24 or 25) with a KpnI restriction enzyme. On the other hand, when a restriction enzyme-treated product of approximately 258 bp (e.g., SEQ ID NO: 26) is formed, the candidate plant is negative for P02.

The positivity for P03 means that only a band of approximately 390 bp long (e.g., SEQ ID NO: 27) is obtained by: performing PCR amplification using a forward primer having the nucleotide sequence shown in SEQ ID NO: 5 and a reverse primer having the nucleotide sequence shown in SEQ ID NO: 6 on the genomic DNA of a candidate plant; and treating the obtained PCR product (approximately 390 bp long) (e.g., SEQ ID NO: 27 or 28) with an AflII restriction enzyme. On the other hand, when a restriction enzyme-treated product of approximately 347 bp (e.g., SEQ ID NO: 29) is formed, the candidate plant is negative for P03.

The positivity for P04 means that only a PCR product of approximately 140 bp (e.g., SEQ ID NO: 30) is formed by performing PCR amplification using a forward primer having the nucleotide sequence shown in SEQ ID NO: 7 and a reverse primer having the nucleotide sequence shown in SEQ ID NO: 8 on the genomic DNA of a candidate plant. When PCR products of 140 bp (e.g., SEQ ID NO: 30) and 158 bp (e.g., SEQ ID NO: 34) are formed, the candidate plant is negative therefor.

The positivity for P05 means that only a band of approximately 288 bp long (e.g., SEQ ID NO: 31) is obtained by: performing PCR amplification using a forward primer having the nucleotide sequence shown in SEQ ID NO: 9 and a reverse primer having the nucleotide sequence shown in SEQ ID NO: 10 on the genomic DNA of a candidate plant; and treating the obtained PCR product (approximately 288 bp long) (e.g., SEQ ID NO: 31 or 32) with a PvuI restriction enzyme. On the other hand, when a restriction enzyme-treated product of approximately 240 bp (e.g., SEQ ID NO: 33) is formed, the candidate plant is negative for P05.

The term "approximately" as to bp long described above means±5 bp. The restriction enzyme treatment can be performed according to conditions recommended by the distributor of each restriction enzyme used.

In the production method of the present invention, "hybridizing" means that the plant of the present invention (first generation (S1)) is crossed with a second plant (S1) to obtain a child plant thereof (plant produced by the production method of the present invention (second generation (S2))). The hybridizing method is preferably backcross. The "backcross" is an approach of further crossing a child plant (S2) generated between the plant of the present invention and the second plant, with the plant of the present invention (i.e., a plant having the genetic feature(s) of the present invention) (S1) to produce a plant having the genetic feature(s) of the present invention. When the second plant (S1) for use in the production method of the present invention has the same phenotype and genetic properties as those of the plant of the present invention, the crossing is substantially backcross. The gene polymorphism of the present invention is inheritable according to the Mendel's law. In association with this, the phenotype correlating with the gene polymorphism, i.e., the high rebaudioside M content phenotype, is also inheritable according to the Mendel's law.

Alternatively, the plant of the present invention can also be produced by selfing. The selfing can be performed by the self-pollination of the stamen pollen of the plant of the present invention with the pistil of the plant of the present invention.

Since the plant produced by the production method of the present invention has the same phenotype and genetic properties as those of the plant of the present invention, the plant produced by the production method of the present invention can be further crossed with a third *stevia* plant to produce a high rebaudioside M content *stevia* plant comprising 2% or more of rebaudioside M with respect to the amount of total steviol glycoside contained in a leaf (e.g., dry leaf or fresh leaf).

In an alternative embodiment, the plant of the present invention may be produced by regenerating a plant by the culture of the tissue culture or the cultured plant cell mentioned above. The culture conditions are the same as those for culturing a tissue culture or a cultured plant cell of the wild type *stevia* plant and are known in the art (Protocols for In Vitro cultures and secondary metabolite analysis of aromatic and medicinal plants, Method in molecular biology, vo. 1391, pp. 113-123).

Alternatively, the plant of the present invention is in a non-genetically modified form and therefore, can also be prepared by integrating the polymorphism described above into the wild type *stevia* plant by a non-genetic modification approach. Examples of the "non-genetic modification approach" include a method of inducing a variation in the gene of a host cell (or a host plant) without transfection with a foreign gene. Examples of such a method include a method of allowing a mutagen to act on a plant cell. Examples of such a mutagen include ethyl methanesulfonate (EMS) and sodium azide. For example, the ethyl methanesulfonate (EMS) can be used at a concentration such as 0.1%, 0.2%, 0.3%, 0.4%, 0.5%, 0.6%, 0.7%, 0.8%, 0.9%, or 1.0% to treat a plant cell. The treatment time is 1 to 48 hours, 2 to 36 hours, 3 to 30 hours, 4 to 28 hours, 5 to 26 hours, or 6 to 24 hours. The procedures themselves of the treatment are known in the art and can be performed by dipping a water-absorbed seed obtained through a water absorption process in a treatment solution containing the mutagen at the concentration described above for the treatment time described above.

An alternative example of the non-genetic modification approach can be a method of irradiating a plant cell with radiation or light beam such as X ray, $\gamma$ ray, or ultraviolet ray. In this case, a cell irradiated using an appropriate dose (ultraviolet lamp intensity, distance, and time) of ultraviolet ray is cultured in a selective medium or the like, and then, a cell, a callus, or a plant having the trait of interest can be selected. In this operation, the irradiation intensity is 0.01 to 100 Gr, 0.03 to 75 Gr, 0.05 to 50 Gr, 0.07 to 25 Gr, 0.09 to 20 Gr, 0.1 to 15 Gr, 0.1 to 10 Gr, 0.5 to 10 Gr, or 1 to 10 Gr. The irradiation distance is 1 cm to 200 m, 5 cm to 100 m, 7 cm to 75 m, 9 cm to 50 m, 10 cm to 30 m, 10 cm to 20 m, or 10 cm to 10 m. The irradiation time is 1 minute to 2 years, 2 minutes to 1 year, 3 minutes to 0.5 years, 4 minutes to 1 month, 5 minutes to 2 weeks, or minutes to 1 week. The irradiation intensity, distance and time differ depending on the type of radiation or the state of the subject to be irradiated (cell, callus, or plant) and can be appropriately adjusted by those skilled in the art.

Approaches such as cell fusion, anther culture (haploid breeding), and remote crossing (haploid breeding) are also known in the art.

In general, plant cells may involve a mutation during culture. Therefore, it is preferred to regenerate a plant individual, for more stably maintaining the trait.

Although the plant of the present invention is a non-genetically modified *stevia* plant, the scope of the present invention does not exclude a plant obtained by the ex-post facto gene recombination (e.g., genome editing) with the plant of the present invention as a host (e.g., a plant further provided with another trait by gene recombination with the plant of the present invention as a host).

3. Method of Screening for Plant of Present Invention

The plant of the present invention or the plant having the same phenotype and genetic properties as those of the plant of the present invention can be screened for by detecting the genetic feature(s) of the present invention from a tissue of this plant. In this context, "screening" means that the plant of the present invention is discriminated from the other plants to select the plant of the present invention.

Thus, in an alternative aspect, the present invention provides a method of screening for a high rebaudioside M content *stevia* plant, comprising a step of detecting the presence and/or the absence of at least one of the following genetic features (1) to (5) the following genetic features from the genome of a test plant (hereinafter, may be referred to as the "screening method of the present invention").

(1) Homozygous for the allele wherein the base at the position corresponding to position 44 of SEQ ID NO:35 is T.
(2) Homozygous for the allele wherein the base at the position corresponding to position 40 of SEQ ID NO:37 is T.
(3) Homozygous for the allele wherein the base at the position corresponding to position 48 of SEQ ID NO:39 is C.

(4) Homozygous for the allele wherein the portion corresponding to positions 55-72 of SEQ ID NO:42 is deleted.

(5) Homozygous for the allele wherein the base at the position corresponding to position 50 of SEQ ID NO:43 is A.

The screening method of the present invention may further comprise a step of selecting from among the test plants a plant in which the presence of at least one genetic feature of (1) to (5) is detected.

The presence of the genetic feature(s) of the present invention can be determined by
  detecting the presence of an allele selected from the group consisting of:
  (A) an allele in which the base at the position corresponding to position 44 of SEQ ID NO: 35 is T;
  (B) an allele in which the base at the position corresponding to position 40 of SEQ ID NO: 37 is T;
  (C) an allele in which the base at the position corresponding to position 48 of SEQ ID NO: 39 is C;
  (D) an allele wherein the portion corresponding to positions 55-72 of SEQ ID NO:42 is deleted; and
  (E) an allele in which the base at the position corresponding to position 50 of SEQ ID NO: 43 is A; and/or
  by detecting the absence of an allele selected from the group consisting of:
  (a) an allele in which the base at the position corresponding to position 44 of SEQ ID NO: 35 is A;
  (b) an allele in which the base at the position corresponding to position 40 of SEQ ID NO: 37 is C;
  (c) an allele in which the base at the position corresponding to position 48 of SEQ ID NO: 39 is G;
  (d) an allele wherein the portion corresponding to positions 55-72 of SEQ ID NO:42 is not deleted; and
  (e) an allele in which the base at the position corresponding to position 50 of SEQ ID NO: 43 is G.

The absence of the genetic feature(s) of the present invention can be determined by
  detecting the absence of an allele selected from the group consisting of:
  (A) an allele in which the base at the position corresponding to position 44 of SEQ ID NO: 35 is T;
  (B) an allele in which the base at the position corresponding to position 40 of SEQ ID NO: 37 is T;
  (C) an allele in which the base at the position corresponding to position 48 of SEQ ID NO: 39 is C;
  (D) an allele wherein the portion corresponding to positions 55-72 of SEQ ID NO:42 is deleted; and
  (E) an allele in which the base at the position corresponding to position 50 of SEQ ID NO: 43 is A; and/or
  detecting the presence of an allele selected from the group consisting of:
  (a) an allele in which the base at the position corresponding to position 44 of SEQ ID NO: 35 is A;
  (b) an allele in which the base at the position corresponding to position 40 of SEQ ID NO: 37 is C;
  (c) an allele in which the base at the position corresponding to position 48 of SEQ ID NO: 39 is G;
  (d) an allele wherein the portion corresponding to positions 55-72 of SEQ ID NO:42 is not deleted; and
  (e) an allele in which the base at the position corresponding to position 50 of SEQ ID NO: 43 is G.

Specific examples of methods of detecting the genetic features of the present invention include, but not limited to, PCR method, TaqMan PCR method, sequencing method, microarray method, Invader method, TILLING method, RAD method, RFLP method, PCR-SSCP method, AFLP method, SSLP method, CAPS method, dCAPS method, ASO method, ARMS method, DGGE method, CCM method, DOL method, MALDI-TOF/MS method, TDI method, padlock probe method, molecular beacon method, DASH method, UCAN method, ECA method, PINPOINT method, PROBE method, VSET method, Survivor assay, Sniper assay, Luminex assay, GOOD method, LCx method, SNaPshot method, Mass ARRAY method, pyrosequencing method, SNP-IT method, melting curve analysis method, etc.

In the case of PCR method, it is preferable to generate a primer such that the 3' end portion has a sequence complementary to the polymorphic site of the present invention. By using a primer designed in this way, the polymerase extension reaction proceeds because the primer hybridizes completely to the template if the template sample has the polymorphism, whereas if the template does not have the variation of the present invention, the extension reaction does not occur because the nucleotide at the 3' end of the primer mismatches the template. Therefore, PCR amplification is performed using such a primer, and the amplification product is analyzed by agarose gel electrophoresis or the like, and if an amplification product of a predetermined size can be confirmed, the template as the sample has a variation, and if the amplification product is not present, it can be judged that the template does not have a variation.

Alternatively, the genetic feature(s) of the present invention can be detected by designing the primer sequence so that the polymorphism of the present invention and the primer sequence do not overlap and the gene variation of the present invention can be PCR amplified, and by sequencing the base sequence of the amplified nucleotide fragment.

For PCR and agarose gel electrophoresis see Sambrook, Fritsch and Maniatis, "Molecular Cloning: A Laboratory Manual" 2nd Edition (1989), Cold Spring Harbor Laboratory Press.

TaqMan PCR method uses fluorescently labeled allele-specific oligos and Taq DNA polymerases (Livak, K. J. Genet). Anal. 14, 143 (1999); Morris T. et al., J. Clin. Microbiol. 34, 2933 (1996)).

The sequencing method is a method of analyzing the presence or absence of a variation by amplifying a region containing the variation by PCR and sequencing the DNA sequence using a Dye Terminator or the like (Sambrook, Fritsch and Maniatis, "Molecular Cloning: A Laboratory Manual" 2nd Edition (1989), Cold Spring Harbor Laboratory Press).

A DNA microarray is one in which one end of a nucleotide probe is immobilized in an array on a support, and includes a DNA chip, a Gene chip, a microchip, a bead array, and the like. By using a probe containing a sequence complementary to the polymorphism of the present invention, the presence or absence of the polymorphism of the present invention can be comprehensively detected. DNA microarray assays such as DNA chips include GeneChip assays (see Affymetrix; U.S. Pat. Nos. 6,045,996; 5,925,525; and 5,858,659). The GeneChip technique utilizes a miniaturized, high density microarray of oligonucleotide probes affixed to a chip.

The invader method combines the hybridization of two reporter probes specific for each allele of a polymorphism such as SNPs and one invader probe to template DNA and the cleavage of DNA by Cleavase enzyme with a special endonuclease activity which cleaves a DNA by recognizing its structure (Livak, K. J. Biomol. Eng. 14, 143-149 (1999); Morris T. et al., J. Clin. Microbiol. 34, 2933 (1996); Lyamichev, V. et al., Science, 260, 778-783 (1993), and the like).

TILLING (Targeting Induced Local Lesions IN Genomes) method is a method in which mutational mismatches in the genomes of a mutagenized mutant population are screened by PCR-amplification and CEL I nuclease-treatment.

In one embodiment, the screening method of the present invention may comprise a step of detecting polymorphic marker positivity from the genome of a test plant. Such a step comprises an operation of extracting genomic DNA from the test plant and detecting the polymorphic marker of the present invention from the genomic DNA. The polymorphic marker is, as already mentioned, at least one member selected from the group consisting of P01 to P05. The polymorphic marker positivity means being positive for at least one marker selected from the group consisting of P01 to P05.

The method of detecting positivity for P01 to P05 is as already mentioned.

In this embodiment, the screening method of the present invention may further comprise a step of selecting a plant in which the polymorphic marker positive of the present invention is detected from among the test plants.

In a certain embodiment, the present invention provides a method of screening for a high rebaudioside M content non-genetically modified *stevia* plant, comprising steps of:

performing PCR amplification using at least one of the following primer sets (1) to (5) on genomic DNA of a test plant; and treating a PCR product obtained by the PCR amplification with a restriction enzyme, and detecting a restriction enzyme-treated product:

(1) a primer set comprising a forward primer comprising the nucleotide sequence shown in SEQ ID NO: 1 and a reverse primer comprising the nucleotide sequence shown in SEQ ID NO: 2;

(2) a primer set comprising a forward primer comprising the nucleotide sequence shown in SEQ ID NO: 3 and a reverse primer comprising the nucleotide sequence shown in SEQ ID NO: 4;

(3) a primer set comprising a forward primer comprising the nucleotide sequence shown in SEQ ID NO: 5 and a reverse primer comprising the nucleotide sequence shown in SEQ ID NO: 6;

(4) a primer set comprising a forward primer comprising the nucleotide sequence shown in SEQ ID NO: 7 and a reverse primer comprising the nucleotide sequence shown in SEQ ID NO: 8; and (5) a primer set comprising a forward primer comprising the nucleotide sequence shown in SEQ ID NO: 9 and a reverse primer comprising the nucleotide sequence shown in SEQ ID NO: 10.

The conditions for the PCR amplification are as already mentioned.

However, the primer set is not limited to those having the sequences of SEQ ID NOs: 1 to 10. For example, the forward primer can have in its 3' end a sequence from the 3' end of SEQ ID NO: 1, 3, 5, 7 or 9 to 15 bases upstream thereof (see the table below), and the reverse primer can have in its 3' end a sequence from the 3' end of SEQ ID NO: 2, 4, 6, 8 or 10 to 15 bases upstream thereof (see the table below). Such a primer may be 15 to 50 bases long or 20 to 45 bases long.

TABLE 1

| poly-morphic marker to be detected | Forward primer (sequence from the 3' end to 15 bases upstream thereof) | Reverse primer (sequence from the 3' end to 15 bases upstream thereof) |
| --- | --- | --- |
| P01(1') | 5'-ATTTATTGTATCTAG-3' (SEQ ID NO: 11) | 5'-GTACACATGCTACAC-3' (SEQ ID NO: 12) |
| P02(2') | 5'-CAAACAACCGGGTAC-3' (SEQ ID NO: 13) | 5'-AGACATTGGCAACTC-3' (SEQ ID NO: 14) |
| P03(3') | 5'-ACGAAACCCGCTTAA-3' (SEQ ID NO: 15) | 5'-TAATCCTTGAATTAG-3' (SEQ ID NO: 16) |
| P04(4') | 5'-ACACGTATACTAATC-3' (SEQ ID NO: 17) | 5'-CATGGTATGTACAAC-3' (SEQ ID NO: 18) |
| P05(5') | 5'-CATTCATGAGCGATC-3' (SEQ ID NO: 19) | 5'-AAATCCCATATGTAG-3' (SEQ ID NO: 20) |

The primer set is not limited to those having the sequences of SEQ ID NOs: 1 to 10. For example, the forward primer can have or comprise a sequence of any 15 or more consecutive bases in SEQ ID NO: 1, 3, 5, 7 or 9, and the reverse primer can have or comprise a sequence of any 15 or more consecutive bases in SEQ ID NO: 2, 4, 6, 8 or 10.

(1") A primer set comprising a forward primer having or comprising a sequence of any 15 or more consecutive bases in SEQ ID NO: 1 and a reverse primer having or comprising a sequence of any 15 or more consecutive bases in SEQ ID NO: 2;

(2") a primer set comprising a forward primer having or comprising a sequence of any 15 or more consecutive bases in SEQ ID NO: 3 and a reverse primer having or comprising a sequence of any 15 or more consecutive bases in SEQ ID NO: 4;

(3") a primer set comprising a forward primer having or comprising a sequence of any 15 or more consecutive bases in SEQ ID NO: 5 and a reverse primer having or comprising a sequence of any 15 or more consecutive bases in SEQ ID NO: 6;

(4") a primer set comprising a forward primer having or comprising a sequence of any 15 or more consecutive bases in SEQ ID NO: 7 and a reverse primer having or comprising a sequence of any 15 or more consecutive bases in SEQ ID NO: 8; or (5") a primer set comprising a forward primer having or comprising a sequence of any 15 or more consecutive bases in SEQ ID NO: 9 and a reverse primer having or comprising a sequence of any 15 or more consecutive bases in SEQ ID NO: 10.

Such a primer may be 15 to 50 bases long, 20 to 45 bases long, or 30 to 65 bases long as long as the arbitrary sequence of 15 or more consecutive bases is present at the 3' end.

The screening methods of the present invention may further comprise a step of determining the RebM content of a tissue (e.g., a leave) of the test *stevia* plant tissue for which the genetic features of the present invention have been detected. The determination of the RebM content is as described in the section relating to the plant of the present invention. In this embodiment, the screening method of the present invention may be applied to daughter plants obtained by selecting individuals with a higher content of RebM from among the test *stevia* plants in which the genetic feature(s) of the present invention is/are detected, and crossing the selected individuals with another *stevia* plants. Thus, the screening method of the present invention may comprise one or more of the following steps.

(i) Detecting the genetic feature(s) of the present invention from the genome of a test *stevia* plant;
(ii) determining the RebM content of the test *stevia* plant tissue in which the genetic feature(s) has/have been detected;
(iii) selecting an individual with a higher content of RebM from among the test *stevia* plants in which the genetic feature(s) of the present invention has/have been detected;
(iv) crossing the selected individual with a higher content of RebM with another *stevia* plant;
(v) detecting the genetic feature(s) of the present invention from the genome of daughter plants obtained by crossing,
(vi) measuring the RebM content of the tissue of the daughter plants in which the genetic feature(s) has/have been detected,
(vii) selecting individuals having a higher RebM content from among the daughter plants in which the genetic features are detected.

Individuals with a high content of RebM of choice may be, for example, up to 50%, up to 40%, up to 30%, up to 20%, up to 10%, up to 5%, up to 4%, up to 3%, up to 2%, or up to 1% of the test *stevia* plants in which the genetic feature(s) of the present invention has/have been detected, with respect to the high content of RebM. Other *stevia* plants to be crossed may or may not contain the genetic feature(s) of the present invention. In the above embodiment, steps (iv) to (vii) can be repeated a plurality of times. In this way, *stevia* plants with a higher content of RebM can be screened.

In the screening method of the present invention, the test *stevia* plant may be a natural plant or a non-transgenic plant. Non-transgenic plants are as described in the section relating to the plant of the present invention.

In the screening method of the present invention, the test *stevia* plant may include a *stevia* plant subjected to a mutagenesis treatment and a progeny plant thereof. The mutagenesis treatment is as described in the section relating to the plant of the present invention, and includes treatment with a mutagen, treatment with radiation or irradiation with light, and the like.

The present invention also provides the above-mentioned primer set, e.g., any one or more primer set(s) selected from the group consisting of the primer sets (1) to (5), (1') to (5') and (1") to (5") above. The present invention further provides a primer set capable of amplifying a region having a base sequence selected from the group consisting of SEQ ID NOs: 35 to 44 by PCR, for example, a forward primer comprising a base sequence of SEQ ID NO: 45, a primer set with a reverse primer comprising a base sequence of SEQ ID NO: 46, a forward primer comprising a base sequence of SEQ ID NO: 47, a primer set with a reverse primer comprising a base sequence of SEQ ID NO: 48, a forward primer comprising a base sequence of SEQ ID NO: 49, a primer set with a reverse primer comprising a base sequence of SEQ ID NO: 50, a forward primer set with a forward primer comprising a base sequence of SEQ ID NO: 51, a primer set with a reverse primer comprising a base sequence of SEQ ID NO: 52, a forward primer comprising a base sequence of SEQ ID NO: 53, and a reverse primer set with a base sequence of SEQ ID NO: 54.

In addition, the present invention provides a probe capable of detecting the presence and/or absence of the genetic features of the present invention, which may be referred to as the "probe of the present invention" hereinafter. The probe of the present invention may have a structure suitable for various detection methods for the presence and/or absence of the genetic feature(s) of the present invention. For example, the probe of the present invention may comprise a base sequence complementary to a portion of a genome comprising a variation site of the present invention. Non-limiting examples of such probes include those comprising a base sequence selected from SEQ ID NOs: 55 to 64. Of these sequences, SEQ ID NOs: 55, 57, 59, 61 and 63 are specific for alleles comprising the variation of the present invention, and SEQ ID NOs: 56, 58, 60, 62 and 64 are specific for alleles not containing the variation of the present invention. The presence of the genetic feature(s) of the present invention may be detected by detection of an allele comprising the variation(s) of the present invention and/or by non-detection of an allele not comprising the variation(s) of the present invention, and the absence of the genetic feature(s) of the invention by non-detection of an allele comprising the variation(s) of the present invention and/or by detection of an allele not comprising the variation(s) of the present invention. The probes of the present invention preferably have a label. Non-limiting examples of such labels include fluorescent labels, luminescent labels, radioactive labels, dyes, enzymes, quenchers, binding moieties with detectable labels, and the like. In a specific embodiment, the probe of the present invention has a base sequence selected from SEQ ID NOs: 55 to 64 and a label.

The present invention further provides a kit for screening comprising any one or more primer set(s) selected from the group consisting of the primer sets (1) to (5), (1') to (5') and (1") to (5"), and optionally a restriction enzyme.

In the kit, the restriction enzyme contained in the kit is XbaI in the case of using any one or more primer set(s) selected from the group consisting of the primer sets (1), (1') and (1").

In the kit, the restriction enzyme contained in the kit is KpnI in the case of using any one or more primer set(s) selected from the group consisting of the primer sets (2), (2') and (2").

In the kit, the restriction enzyme contained in the kit is AflII in the case of using any one or more primer set(s) selected from the group consisting of the primer sets (3), (3') and (3").

In the kit, the restriction enzyme contained in the kit is PvuI in the case of using any one or more primer set(s) selected from the group consisting of the primer sets (5), (5') and (5").

In another embodiment of the kit:
in case the primer set comprises a forward primer having or comprising a sequence of any contiguous 15 bases or more in SEQ ID NO: 1, the restriction enzyme comprises XbaI;
in case the primer set comprises a forward primer having or comprising a sequence of any consecutive 15 bases or more in SEQ ID NO:3, the restriction enzyme comprises KpnI;
in case the primer set comprises a forward primer having or comprising a sequence of any consecutive 15 bases or more in SEQ ID NO:5, the restriction enzyme comprises AflII; and
in case the primer set comprises a forward primer having or comprising a sequence of any consecutive 15 bases or more in SEQ ID NO: 9, the restriction enzyme comprises PvuI.

The present invention also provides a screening kit comprising a primer set capable of amplifying by PCR a region having a base sequence selected from the group consisting of SEQ ID NOs: 35 to 44, and a probe of the present invention.

These primer sets, probes and kits can be used to detect the genetic feature(s) of the present invention, used in the screening methods of the present invention, and the like. These primer sets and kits may also comprise an instruction including an explanation on the detection of genetic feature(s) of the present invention and on the screening method of the present invention, e.g., a written instruction, and media, e.g., a flexible disk, a CD, a DVD, a Blu-ray disk, a memory card, a USB memory, etc., having recorded thereon information regarding the method of use.

5. Method of Producing Extract Derived from Plant and Product Comprising the Extract In a further aspect, the present invention provides a method of producing a rebaudioside M-containing extract, comprising a step of obtaining an extract from the plant of the present invention, or a seed or a leaf (e.g., dry leaf or fresh leaf) of the plant (hereinafter, may be referred to as the "extract production method of the present invention"). The present invention further provides a method of producing rebaudioside M, comprising a step of purifying rebaudioside M from an extract obtained by the extract production method of the present invention (hereinafter, may be referred to as the "rebaudioside M production method of the present invention").

Specifically, the present invention provides a method of producing rebaudioside M or rebaudioside D, or both, comprising a step of obtaining an extract containing rebaudioside M or rebaudioside D, or both from the high rebaudioside M content *stevia* plant of the present invention, the high rebaudioside M content *stevia* plant screened for by the screening method of the present invention, or the high rebaudioside M content *stevia* plant produced by the method of the present invention.

The extract containing rebaudioside M or rebaudioside D, or both can be obtained by reacting a fresh leaf or a dry leaf of the plant of the present invention with a suitable solvent (an aqueous solvent such as water or an organic solvent such as an alcohol, ether or acetone). For the extraction conditions, etc., see a method described in Ohta et al., J. Appl. Glycosci., Vol. 57, No. 3 (2010) or WO2010/038911, or a method described in Examples mentioned later.

The rebaudioside M or the rebaudioside D, or both can be purified from the extract containing rebaudioside M or rebaudioside D, or both by use of a method known in the art such as a gradient of ethyl acetate or any of other organic solvents:water, high performance liquid chromatography (HPLC), gas chromatography, time-of-flight mass spectrometry (TOF-MS), or ultra (high) performance liquid chromatography (UPLC).

The extract obtained by the extract production method of the present invention (hereinafter, may be referred to as the "extract of the present invention") comprises rebaudioside M or rebaudioside D, or both at higher content as compared with the wild type *stevia* species.

The extract of the present invention may comprise rebaudioside M or rebaudioside D, or both at higher content by 300% or more, 400% or more, 500% or more, 600% or more, 700% or more, 800% or more, 900% or more, 1100% or more, 1200% or more, 1300% or more, 1400% or more, 1500% or more, 1600% or more, 1700% or more, 1800% or more, 1900% or more, 2000% or more, 2100% or more, 2200% or more, 2300% or more, 2400% or more, 2500% or more, 2600% or more, 2700% or more, 2800% or more, 2900% or more, 3000% or more, 3100% or more, 3200% or more, 3300% or more, 3400% or more, 3500% or more, 3600% or more, 3700% or more, 3800% or more, 3900% or more, 4000% or more, 4100% or more, 4200% or more, 4300% or more, 4400% or more, 4500% or more, 4600% or more, 4700% or more, 4800% or more, 4900% or more, or 5000% or more as compared with an extract obtained from the wild type *stevia* species. The extract of the present invention and the extract obtained from the wild type *stevia* species may be those obtained by the same process.

The extract of the present invention thus obtained and/or rebaudioside M or rebaudioside D, or both obtained by the method of producing rebaudioside M or rebaudioside D, or both according to the present invention can be mixed with other components to produce a novel medicament, flavor or food or drink product with increased content of rebaudioside M or rebaudioside D, or both. Accordingly, in an alternative aspect, the present invention provides a method of producing a medicament, a flavor or a food or drink product, comprising a step of mixing the extract of the present invention and/or rebaudioside M or rebaudioside D, or both obtained by the method of producing rebaudioside M or rebaudioside D, or both according to the present invention with other components. The present invention further provides a novel medicament, flavor or food or drink product with increased content of rebaudioside M or rebaudioside D, or both, obtained by the production method. In this context, the food or drink product means a drink and a food. Thus, in a certain embodiment, the present invention provides a novel medicament, flavor, drink or food and also provides a method of producing the medicament, the flavor, the drink or the food.

EXAMPLES

Hereinafter, the present invention will be described with reference to Experimental Examples, Examples, etc. However, the present invention is not limited by these specific embodiments.

[Example 1] Preparation of *Stevia* Plant with High RebM Content

1. Introduction of Breeding Material and Initial Selection

Commercially available *stevia* seeds were seeded, and raised in August 2014, and about 3,000 individuals were subjected to selection based on the development and growth condition and the foliar morphology during the period of October 2014 to March 2015. The content and content ratio of each steviol glycoside of 115 individuals selected in April 2015 were measured by quantitative analysis using LC-MS/MS, and 3 individuals each having a high RebD and RebM content ratio (in each individual, the rate of the total content of the two components to the total steviol glycoside (TSG) content was 20% or more) were selected. Simultaneously, selection based on the total steviol glycoside (TSG) content was also carried out, and 14 individuals having a TSG yield (the total amount of measurable steviol glycosides per unit dry-leaf weight) of 20% or more were selected.

2. Production and Selection of Selfed Lines)

From the 115 individuals selected above, 5 high RebA type individuals each exhibiting good development were selected. Inter-individual or intra-individual artificial pollination was started in January 2015, and mass seed production was performed in March 2015 to obtain the first selfed generation (S1 seeds). Furthermore, the S1 seeds were seeded and raised, and S1 populations of 105 individuals were obtained. In June 2015, each individual of these S1 populations was separately grown to obtain the second selfed generations (S2 seeds) by intra-individual artificial pollination. The resulting S2 seeds were distinguished between the respective S1 individuals as lines to obtain S2 populations of 105 lines. Subsequently, the resulting S2 individuals were investigated for the development and growth condition, and four leaves were sampled from each individual exhibiting good development and growth were subjected to quantitative analysis of the amount of steviol glycosides using LC-MS/MS. The RebD content, RebM content, and TSG content were calculated from the analytical results obtained. An individual with the sum of the RebD content and the RebM content per 100 g of leaves being higher than 2 g (=2%) was selected as an excellent individual.

3. Production and Selection of Hybrid Lines)

Plants with high RebD and RebM content (3 individuals) and plants with high TSG content (6 individuals) selected by component analysis were subjected, as mother plants for breeding, to a crossing test involving 53 combinations in total. The selected individuals were vegetatively propagated by cutting in April 2015 to establish seedlings in June 2015, which were then matured until November 2015 to establish a plurality of mother stocks of each individual. Artificial crossing was started in January 2016, and about 1,000 hybrid seeds (F1 seeds) for each combination were obtained. Thereafter, seeding and raising of the resulting F1 seeds were started in March 2015. Subsequently, the resulting F1 individuals were investigated for the development and growth condition, and four leaves were sampled from each individual exhibiting good development and growth and were subjected to quantitative analysis of the amount of steviol glycosides using LC-MS/MS. The RebD content, RebM content, and TSG content were calculated from the analytical results obtained. An individual the sum of the RebD content and the RebM content of which was higher than 2 g/100 g (=2%) was selected as an excellent individual.

4. Preparation of Genetic Marker

Genetic markers were prepared using 10 individuals obtained in the initial selection. The individuals were classified in June 2015 into 2 groups, i.e., a high content group (29.16% or more) and a low content group (6.06% or less), on the basis of the sum of the RebD and RebM content ratios. Search for polymorphism common in each group was carried out in a WRKY coding region and a WD40 coding region known to activate the biosynthesis pathway of a secondary metabolite to obtain particular single nucleotide polymorphism (SNP). Primer design and restriction enzyme selection were performed on the basis of the obtained SNP to establish polymorphic markers (1) to (5) that enabled the identification of the particular SNP.

(1) P01

For the detection of the marker P01, PCR was performed using the primers given below. A restriction enzyme (XbaI) was added to the PCR product, and enzymatic reaction was performed at 37° C. for treatment with the restriction enzyme. After the restriction enzyme treatment, electrophoresis was performed using a microchip type electrophoresis apparatus LabChip GX Touch HT. The marker was identified on the basis of a band pattern after the electrophoresis.

The primer sequences are as follows.

```
Fw primer:
                                          (SEQ ID NO: 1)
5'-AAGGTTCTTTATTTTTAAACTTATGTTAATTTATTGTATCTAG-3'

Rv primer:
                                          (SEQ ID NO: 2)
5'-CCTTATGTACACATGCTACAC-3'
```

When a restriction enzyme-treated product of approximately 344 bp (e.g., SEQ ID NO: 23) was not formed by the XbaI restriction enzyme treatment of the obtained PCR product (approximately 383 bp long), the test subject was regarded as being positive for P01.

(2) P02

For the detection of the marker P02, PCR was performed using the primers given below. A restriction enzyme (KpnI) was added to the PCR product, and enzymatic reaction was performed at 37° C. for treatment with the restriction enzyme. After the restriction enzyme treatment, electrophoresis was performed using a microchip type electrophoresis apparatus LabChip GX Touch HT. The marker was identified on the basis of a band pattern after the electrophoresis.

The primer sequences are as follows.

```
Fw primer:
                                          (SEQ ID NO: 3)
5'-TAATCATCCAAACCCTAATCTCGCCAAACAACCGGGTAC-3'

Rv primer:
                                          (SEQ ID NO: 4)
5'-GAGGAAGACATTGGCAACTC-3'
```

When a restriction enzyme-treated product of approximately 260 bp (e.g., SEQ ID NO: 26) was not formed by the KpnI restriction enzyme treatment of the obtained PCR product (approximately 297 bp long), the test subject was regarded as being positive for P02.

(3) P03

For the detection of the marker P03, PCR was performed using the primers given below. A restriction enzyme (AflII) was added to the PCR product, and enzymatic reaction was performed at 37° C. for treatment with the restriction enzyme. After the restriction enzyme treatment, electrophoresis was performed using a microchip type electrophoresis apparatus LabChip GX Touch HT. The marker was identified on the basis of a band pattern after the electrophoresis.

The primer sequences are as follows.

```
Fw primer:
                                          (SEQ ID NO: 5)
5'-CGATGGTTTTTGCTACATGAAAACCCTAGAAGACG
AAACCCGCTTAA-3'

Rv primer:
                                          (SEQ ID NO: 6)
5'-ACCAGCAATAATCCTTGAATTAG-3'
```

When a restriction enzyme-treated product of approximately 347 bp (e.g., SEQ ID NO: 29) was not formed by the AflII restriction enzyme treatment of the obtained PCR product (approximately 390 bp long), the test subject was regarded as being positive for P03.

(4) P04

For the detection of the marker P04, PCR was performed using the primers given below. The PCR product was electrophoresed using a microchip type electrophoresis apparatus LabChip GX Touch HT. The marker was identified on the basis of a band pattern after the electrophoresis.

The primer sequences are as follows.

```
Fw primer:
                                      (SEQ ID NO: 7)
5'-CGCAAACACGTATACTAATC-3'

Rv primer:
                                      (SEQ ID NO: 8)
5'-TTTAGCATGGTATGTACAAC-3'
```

When only a PCR product of approximately 140 bp (e.g., SEQ ID NO: 30) was formed, the test subject was regarded as being positive for P04.

(5) P05

For the detection of the marker P05, PCR was performed using the primers given below. A restriction enzyme (PvuI) was added to the PCR product, and enzymatic reaction was performed at 37° C. for treatment with the restriction enzyme. After the restriction enzyme treatment, electrophoresis was performed using a microchip type electrophoresis apparatus LabChip GX Touch HT. The marker was identified on the basis of a band pattern after the electrophoresis.

The primer sequences are as follows.

```
Fw primer:
                                      (SEQ ID NO: 9)
5'-ATACAAAAACACAACCCATATGGTCAAATCAA

CCCATTCATGAGCGATC-3'

Rv primer:
                                      (SEQ ID NO: 10)
5'-CCCTTGTAAATCCCATATGTAG-3'
```

When a restriction enzyme-treated product of approximately 240 bp (e.g., SEQ ID NO: 33) was not formed by the PvuI restriction enzyme treatment of the obtained PCR product (approximately 288 bp long), the test subject was regarded as being positive for P05.

5. Verification of Genetic Marker

A marker verification experiment was carried out using the polymorphic markers established above and individual group I. Component analysis was conducted on 192 individuals of individual group I, and top 8 individuals (0.35% or more) and bottom 8 individuals (0.12% or less) were selected on the basis of RebM content values, followed by the marker test as described above. As a result, only the top 8 individuals with high content of RebM were selected as individuals positive for the polymorphism of interest (FIG. 1).

Figure 2:
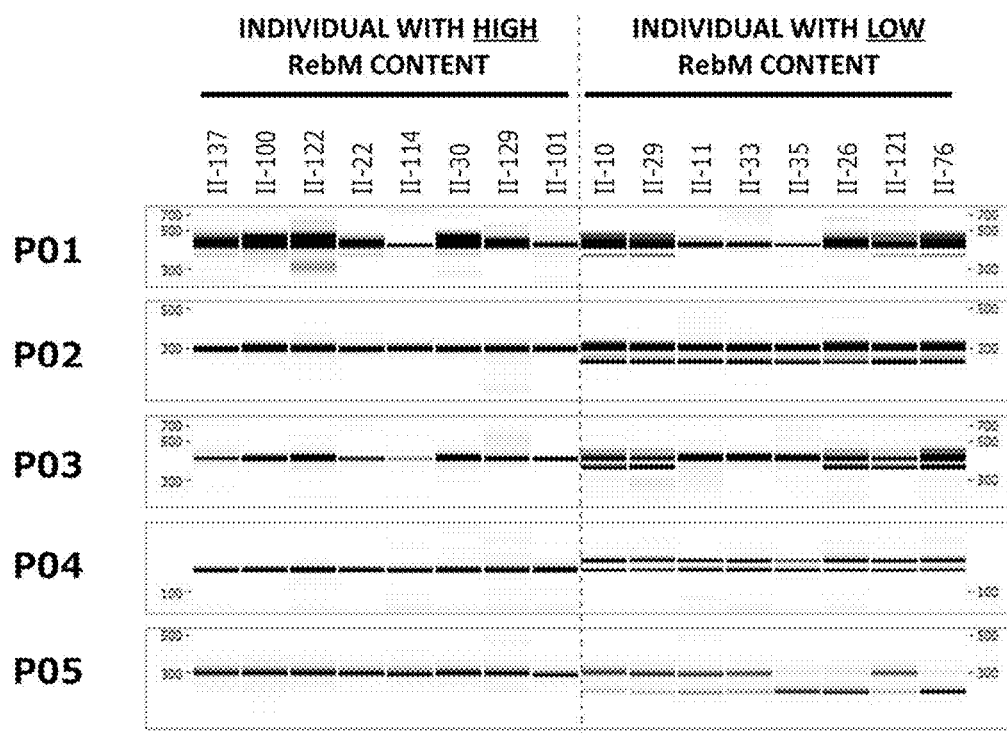
FIG. 2 shows electrophoresis images obtained in the marker detection of individual group II.

The verification test was also conducted on individual group II in the same way as above. Component analysis was conducted on 137 individuals of individual group II, and top 8 individuals (0.24% or more) and bottom 8 individuals (0.01% or less) were selected on the basis of RebM content values, followed by the marker test. As a result, only the top 8 individuals with high content of RebM were selected as individuals having the polymorphism of interest (FIG. 2). As is evident from FIGS. 1 and 2, the band having the size of interest appeared only in individuals having a high RebM phenotype.

6. Increase in the Number of Members in Sample Population

An experiment was conducted for further verification using the increased number of individuals in the two segregating populations used in the verification of the genetic markers, i.e., individual groups I and II. 62 individuals and 109 individuals, respectively, including the numbers of individuals described above were used. Each individual group was divided on the basis of RebM content into 3 groups: 0.2% or more, 0.1% or more to less than 0.2%, and 0% or more to less than 0.1%. As a result of conducting the marker test, the group of 0.2% or more was preferentially detected with the marker of the present invention. These results demonstrated that the frequency of appearance of positive individuals was statistically significantly different among groups (goodness of fit test by the chi square test; the null hypothesis stated that the frequency distribution was even without the association of the marker test results with the phenotype; for the test results, see the tables below).

TABLE 2

Results of marker test on individual group I (62 individuals)
Marker used: P02

| RebM content (%) | Test results | | |
|---|---|---|---|
| | Positive | Negative | Total |
| 0.2 or more | 29 | 8 | 37 |
| 0.1 or more and less than 0.2 | 0 | 20 | 20 |
| 0 or more and less than 0.1 | 0 | 5 | 5 |
| Total | 29 | 33 | 62 |

Chi square test result (df = 2) 36.81**

TABLE 3

Results of marker test on individual group I (62 individuals)
Marker used: P05

| RebM content (%) | Test results | | |
|---|---|---|---|
| | Positive | Negative | Total |
| 0.2 or more | 29 | 8 | 37 |
| 0.1 or more and less than 0.2 | 0 | 20 | 20 |
| 0 or more and less than 0.1 | 0 | 5 | 5 |
| Total | 29 | 33 | 62 |

Chi square test result (df = 2) 36.81**

TABLE 4

Results of marker test on individual group II (109 individuals)
Marker used: P02

| RebM content (%) | Test results | | |
|---|---|---|---|
| | Positive | Negative | Total |
| 0.2 or more | 18 | 1 | 19 |
| 0.1 or more and less than 0.2 | 35 | 3 | 38 |
| 0 or more and less than 0.1 | 5 | 47 | 52 |
| Total | 58 | 51 | 109 |

Chi square test result (df = 2) 75.94**

TABLE 5

Results of marker test on individual group II (109 individuals)
Marker used: P05

| RebM content (%) | Test results | | |
|---|---|---|---|
| | Positive | Negative | Total |
| 0.2 or more | 9 | 10 | 19 |
| 0.1 or more and less than 0.2 | 10 | 28 | 38 |
| 0 or more and less than 0.1 | 2 | 50 | 52 |
| Total | 21 | 88 | 109 |

Chi square test result (df = 2) 18.81**

7. Selection of Plant with High RebM Content

As a result of selecting a plant with high RebM content using the genetic markers obtained above, individuals having a RebM ratio of 2% or more were also able to be selected in segregating populations other than the populations for verification, as shown in the table below, confirming that these genetic markers are capable of serving as practical selection markers. The results of selecting a plant with high RebM content are shown in the table below. In the table, the circle mark represents that the marker test results were positive.

TABLE 6

| Line No. | TSG (%) | RebA Content (%) | RA/TSG | RebD Content (%) | RD/TSG | RebM Content (%) | RM/TSG | RebA + RebM Content (%) | RAM/TSG |
|---|---|---|---|---|---|---|---|---|---|
| S1736 | 18.45 | 13.23 | 71.73% | 1.77 | 9.58% | 1.46 | 7.92% | 14.69 | 79.65% |
| S7518 | 15.10 | 7.20 | 47.64% | 3.57 | 23.64% | 1.29 | 8.56% | 8.49 | 56.20% |
| S21718 | 8.96 | 5.59 | 62.37% | 1.42 | 15.85% | 1.19 | 13.31% | 6.78 | 75.68% |
| S21708 | 9.12 | 6.07 | 66.53% | 1.09 | 11.91% | 1.11 | 12.14% | 7.18 | 78.67% |
| S1749 | 7.40 | 4.16 | 56.20% | 1.42 | 19.23% | 1.07 | 14.49% | 5.23 | 70.69% |
| S21817 | 7.27 | 4.46 | 61.32% | 1.13 | 15.50% | 1.03 | 14.11% | 5.49 | 75.43% |
| S21745 | 9.53 | 6.31 | 66.22% | 1.32 | 13.83% | 0.97 | 10.13% | 7.28 | 76.36% |
| S21706 | 8.77 | 5.26 | 59.97% | 1.61 | 18.30% | 0.96 | 11.00% | 6.22 | 70.97% |
| S21714 | 9.26 | 5.47 | 59.06% | 1.97 | 21.30% | 0.94 | 10.10% | 6.41 | 69.16% |
| S21707 | 9.76 | 6.23 | 63.82% | 1.57 | 16.09% | 0.92 | 9.45% | 7.15 | 73.27% |
| S21750 | 8.11 | 5.21 | 64.25% | 1.15 | 14.20% | 0.90 | 11.13% | 6.11 | 75.38% |
| S21751 | 8.28 | 5.32 | 64.24% | 1.27 | 15.32% | 0.90 | 10.89% | 6.22 | 75.13% |
| S7535 | 11.61 | 6.54 | 56.35% | 2.25 | 19.42% | 0.90 | 7.75% | 7.44 | 64.10% |
| S21818 | 7.05 | 4.32 | 61.28% | 1.14 | 16.16% | 0.89 | 12.66% | 5.21 | 73.94% |
| S21746 | 8.66 | 5.19 | 59.91% | 1.68 | 19.34% | 0.89 | 10.27% | 6.08 | 70.18% |
| S751 | 9.83 | 5.46 | 55.57% | 2.16 | 21.96% | 0.87 | 8.88% | 6.33 | 64.44% |
| S21796 | 8.27 | 5.30 | 64.08% | 1.33 | 16.11% | 0.85 | 10.30% | 6.15 | 74.38% |
| S7567 | 7.86 | 3.92 | 49.84% | 2.15 | 27.30% | 0.85 | 10.79% | 4.77 | 60.63% |
| S21811 | 9.22 | 6.03 | 65.43% | 1.42 | 15.41% | 0.85 | 9.19% | 6.88 | 74.62% |
| S21742 | 9.37 | 6.39 | 68.22% | 1.35 | 14.36% | 0.74 | 7.93% | 7.13 | 76.15% |
| S1753 | 6.70 | 3.60 | 53.75% | 1.68 | 25.08% | 0.66 | 9.78% | 4.26 | 63.54% |
| S7565 | 8.91 | 3.21 | 36.02% | 2.77 | 31.11% | 0.53 | 5.96% | 3.74 | 41.98% |
| S21361 | 18.28 | 11.97 | 65.48% | 2.52 | 13.81% | 0.46 | 2.51% | 12.43 | 67.99% |
| S21355 | 15.09 | 9.78 | 64.80% | 1.84 | 12.20% | 0.35 | 2.34% | 10.13 | 67.15% |
| S21356 | 13.09 | 7.83 | 59.84% | 2.16 | 16.49% | 0.31 | 2.36% | 8.14 | 62.20% |
| S21357 | 13.66 | 9.24 | 67.64% | 1.66 | 12.18% | 0.30 | 2.21% | 9.54 | 69.85% |
| S21375 | 14.04 | 8.61 | 61.33% | 2.32 | 16.50% | 0.30 | 2.12% | 8.91 | 63.45% |
| S21369 | 12.66 | 7.89 | 62.34% | 1.58 | 12.49% | 0.29 | 2.25% | 8.18 | 64.60% |
| S21360 | 12.68 | 7.86 | 61.98% | 1.82 | 14.31% | 0.29 | 2.25% | 8.15 | 64.22% |
| S21358 | 10.48 | 6.28 | 59.95% | 1.68 | 16.06% | 0.27 | 2.57% | 6.55 | 62.52% |
| S1785 | 5.50 | 1.94 | 35.25% | 1.61 | 29.18% | 0.24 | 4.39% | 2.18 | 39.64% |
| S14252 | 6.93 | 2.06 | 29.74% | 1.66 | 23.99% | 0.21 | 3.02% | 2.27 | 32.77% |
| S17197 | 7.97 | 2.65 | 33.26% | 1.72 | 21.59% | 0.19 | 2.37% | 2.84 | 35.63% |
| S21314 | 11.68 | 7.57 | 64.83% | 0.10 | 0.85% | 0.04 | 0.33% | 7.61 | 65.15% |
| S1552 | 13.20 | 8.94 | 67.72% | 0.09 | 0.71% | 0.04 | 0.27% | 8.97 | 67.99% |
| S21297 | 11.57 | 6.90 | 59.66% | 0.11 | 0.91% | 0.03 | 0.26% | 6.93 | 59.92% |
| S1357 | 10.43 | 6.04 | 57.89% | 0.11 | 1.03% | 0.03 | 0.25% | 6.06 | 58.14% |
| S7548 | 11.30 | 3.48 | 30.82% | 0.08 | 0.69% | 0.01 | 0.06% | 3.49 | 30.88% |

| Line No. | RebD + RebM Content (%) | RDM/TSG | RebM/RebA | RebM/RebD | P01 | P02 | P03 | P04 | P05 |
|---|---|---|---|---|---|---|---|---|---|
| S1736 | 3.23 | 17.51% | 0.11 | 0.83 | ○ | ○ | ○ | ○ | ○ |
| S7518 | 4.86 | 32.19% | 0.18 | 0.36 | ○ | ○ | ○ | ○ | ○ |
| S21718 | 2.61 | 29.16% | 0.21 | 0.84 | ○ | ○ | ○ | ○ | ○ |
| S21708 | 2.19 | 24.05% | 0.18 | 1.02 | ○ | ○ | ○ | ○ | ○ |
| S1749 | 2.50 | 33.73% | 0.26 | 0.75 | ○ | ○ | ○ | ○ | ○ |
| S21817 | 2.15 | 29.61% | 0.23 | 0.91 | ○ | ○ | ○ | ○ | ○ |
| S21745 | 2.28 | 23.96% | 0.15 | 0.73 | ○ | | ○ | ○ | ○ |
| S21706 | 2.57 | 29.30% | 0.18 | 0.60 | | | | | ○ |
| S21714 | 2.91 | 31.40% | 0.17 | 0.47 | ○ | ○ | ○ | ○ | ○ |
| S21707 | 2.49 | 25.54% | 0.15 | 0.59 | ○ | ○ | ○ | ○ | ○ |

TABLE 6-continued

| | | | | | | | | | |
|---|---|---|---|---|---|---|---|---|---|
| S21750 | 2.05 | 25.33% | 0.17 | 0.78 | ○ | ○ | ○ | ○ | ○ |
| S21751 | 2.17 | 26.21% | 0.17 | 0.71 | ○ | ○ | ○ | ○ | ○ |
| S7535 | 3.15 | 27.17% | 0.14 | 0.40 | ○ | ○ | ○ | ○ | ○ |
| S21818 | 2.03 | 28.82% | 0.21 | 0.78 | ○ | ○ | ○ | ○ | ○ |
| S21746 | 2.57 | 29.61% | 0.17 | 0.53 | ○ | ○ | ○ | ○ | ○ |
| S751 | 3.03 | 30.84% | 0.16 | 0.40 | ○ | ○ | ○ | ○ | |
| S21796 | 2.18 | 26.41% | 0.16 | 0.64 | ○ | ○ | ○ | ○ | ○ |
| S7567 | 2.99 | 38.09% | 0.22 | 0.40 | ○ | ○ | ○ | ○ | ○ |
| S21811 | 2.27 | 24.61% | 0.14 | 0.60 | ○ | ○ | ○ | ○ | ○ |
| S21742 | 2.09 | 22.30% | 0.12 | 0.55 | ○ | ○ | ○ | ○ | ○ |
| S1753 | 2.33 | 34.86% | 0.18 | 0.39 | ○ | ○ | ○ | ○ | ○ |
| S7565 | 3.30 | 37.07% | 0.17 | 0.19 | ○ | ○ | ○ | ○ | |
| S21361 | 2.98 | 16.33% | 0.04 | 0.18 | ○ | ○ | ○ | ○ | ○ |
| S21355 | 2.20 | 14.55% | 0.04 | 0.19 | ○ | ○ | ○ | ○ | ○ |
| S21356 | 2.47 | 18.85% | 0.04 | 0.14 | ○ | ○ | ○ | ○ | ○ |
| S21357 | 1.97 | 14.39% | 0.03 | 0.18 | ○ | ○ | ○ | ○ | ○ |
| S21375 | 2.61 | 18.62% | 0.03 | 0.13 | ○ | ○ | ○ | ○ | ○ |
| S21369 | 1.87 | 14.74% | 0.04 | 0.18 | ○ | ○ | ○ | ○ | ○ |
| S21360 | 2.10 | 16.56% | 0.04 | 0.16 | ○ | ○ | ○ | ○ | ○ |
| S21358 | 1.95 | 18.64% | 0.04 | 0.16 | ○ | ○ | ○ | ○ | ○ |
| S1785 | 1.85 | 33.57% | 0.12 | 0.15 | ○ | ○ | ○ | ○ | ○ |
| S14252 | 1.87 | 27.01% | 0.10 | 0.13 | ○ | ○ | ○ | ○ | |
| S17197 | 1.91 | 23.97% | 0.07 | 0.11 | ○ | ○ | ○ | ○ | ○ |
| S21314 | 0.14 | 1.17% | 0.01 | 0.38 | | | | | |
| S1552 | 0.13 | 0.98% | 0.00 | 0.38 | | | | | |
| S21297 | 0.14 | 1.17% | 0.00 | 0.28 | | | | | |
| S1357 | 0.13 | 1.28% | 0.00 | 0.24 | | | | | |
| S7548 | 0.09 | 0.75% | 0.00 | 0.09 | | | | | |

INDUSTRIAL APPLICABILITY

The present invention enables the more efficient provision of rebaudioside M and rebaudioside D and can therefore provide a medicament, a flavor or a food or drink product, etc. comprising sufficient amounts of rebaudioside M and rebaudioside D and thereby having good quality of taste.

The invention claimed is:

1. A high rebaudioside M content non-genetically modified *stevia* plant comprising 1.19 g to 1.46 g of rebaudioside M per 100 g of a dry leaf, and having the following genetic features (1) to (5):
   (1) homozygous for the allele wherein the base at the position corresponding to position 44 of SEQ ID NO:35 is T;
   (2) homozygous for the allele wherein the base at the position corresponding to position 40 of SEQ ID NO:37 is T;
   (3) homozygous for the allele wherein the base at the position corresponding to position 48 of SEQ ID NO:39 is C;
   (4) homozygous for the allele wherein the portion corresponding to positions 55-72 of SEQ ID NO:42 is deleted; and
   (5) homozygous for the allele wherein the base at the position corresponding to position 50 of SEQ ID NO:43 is A.

2. A seed, a tissue, a tissue culture or a cultured plant cell of the plant according to claim 1.

3. The tissue, tissue culture or the cultured plant cell according to claim 2, which is an embryo, a meristem cell, a pollen, a leaf, a root, a root apex, a petal, a protoplast, a leaf section or a callus.

4. A method of producing a high rebaudioside M content *stevia* plant comprising 1.19 g to 1.46 g of rebaudioside M per 100 g of a dry leaf, the method comprising crossing the *stevia* plant according to claim 1 with a second *stevia* plant, wherein the second plant is optionally a non-genetically modified *stevia* plant comprising 1.19 g to 1.46 g of rebaudioside M per 100 g of a dry leaf.

5. A method of producing a rebaudioside M-containing extract, comprising obtaining an extract from the plant according to claim 1.

6. A method of producing rebaudioside M, comprising obtaining a rebaudioside M-containing extract from the plant according to claim 1, and purifying rebaudioside M from the rebaudioside M-containing extract.

7. A method of producing a food or drink product, a sweetener composition, a flavor or a medicament, comprising obtaining a rebaudioside M-containing extract from the plant according to claim 1, and mixing the extract with other components.

* * * * *

```
                           SEQUENCE LISTING

<160> NUMBER OF SEQ ID NOS: 84

<210> SEQ ID NO 1
<211> LENGTH: 43
<212> TYPE: DNA
<213> ORGANISM: Artificial Sequence
<220> FEATURE:
<223> OTHER INFORMATION: Synthetic DNA

<400> SEQUENCE: 1
aaggttcttt atttttaaac ttatgttaat ttattgtatc tag              43

<210> SEQ ID NO 2
<211> LENGTH: 21
<212> TYPE: DNA
<213> ORGANISM: Artificial Sequence
<220> FEATURE:
<223> OTHER INFORMATION: Synthetic DNA

<400> SEQUENCE: 2
ccttatgtac acatgctaca c                                      21

<210> SEQ ID NO 3
<211> LENGTH: 39
<212> TYPE: DNA
<213> ORGANISM: Artificial Sequence
<220> FEATURE:
<223> OTHER INFORMATION: Synthetic DNA

<400> SEQUENCE: 3
```
taatcatcca aaccctaatc tcgccaaaca accgggtac        39

<210> SEQ ID NO 4
<211> LENGTH: 20
<212> TYPE: DNA
<213> ORGANISM: Artificial Sequence
<220> FEATURE:
<223> OTHER INFORMATION: Synthetic DNA

<400> SEQUENCE: 4
gaggaagaca ttggcaactc        20

<210> SEQ ID NO 5
<211> LENGTH: 47
<212> TYPE: DNA
<213> ORGANISM: Artificial Sequence
<220> FEATURE:
<223> OTHER INFORMATION: Synthetic DNA

<400> SEQUENCE: 5
cgatggtttt tgctacatga aaccctaga agacgaaacc cgcttaa        47

<210> SEQ ID NO 6
<211> LENGTH: 23
<212> TYPE: DNA
<213> ORGANISM: Artificial Sequence
<220> FEATURE:
<223> OTHER INFORMATION: Synthetic DNA

<400> SEQUENCE: 6
accagcaata atccttgaat tag        23

<210> SEQ ID NO 7
<211> LENGTH: 20
<212> TYPE: DNA
<213> ORGANISM: Artificial Sequence
<220> FEATURE:
<223> OTHER INFORMATION: Synthetic DNA

<400> SEQUENCE: 7
cgcaaacacg tatactaatc        20

<210> SEQ ID NO 8
<211> LENGTH: 20
<212> TYPE: DNA
<213> ORGANISM: Artificial Sequence
<220> FEATURE:
<223> OTHER INFORMATION: Synthetic DNA

<400> SEQUENCE: 8
tttagcatgg tatgtacaac        20

<210> SEQ ID NO 9
<211> LENGTH: 49
<212> TYPE: DNA
<213> ORGANISM: Artificial Sequence
<220> FEATURE:
<223> OTHER INFORMATION: Synthetic DNA

<400> SEQUENCE: 9
atacaaaaac acaacccata tggtcaaatc aacccattca tgagcgatc        49

<210> SEQ ID NO 10
<211> LENGTH: 22
<212> TYPE: DNA
<213> ORGANISM: Artificial Sequence

```
<220> FEATURE:
<223> OTHER INFORMATION: Synthetic DNA

<400> SEQUENCE: 10
cccttgtaaa tcccatatgt ag                                              22

<210> SEQ ID NO 11
<211> LENGTH: 15
<212> TYPE: DNA
<213> ORGANISM: Artificial Sequence
<220> FEATURE:
<223> OTHER INFORMATION: Synthetic DNA

<400> SEQUENCE: 11
atttattgta tctag                                                      15

<210> SEQ ID NO 12
<211> LENGTH: 15
<212> TYPE: DNA
<213> ORGANISM: Artificial Sequence
<220> FEATURE:
<223> OTHER INFORMATION: Synthetic DNA

<400> SEQUENCE: 12
gtacacatgc tacac                                                      15

<210> SEQ ID NO 13
<211> LENGTH: 15
<212> TYPE: DNA
<213> ORGANISM: Artificial Sequence
<220> FEATURE:
<223> OTHER INFORMATION: Synthetic DNA

<400> SEQUENCE: 13
caaacaaccg ggtac                                                      15

<210> SEQ ID NO 14
<211> LENGTH: 15
<212> TYPE: DNA
<213> ORGANISM: Artificial Sequence
<220> FEATURE:
<223> OTHER INFORMATION: Synthetic DNA

<400> SEQUENCE: 14
agacattggc aactc                                                      15

<210> SEQ ID NO 15
<211> LENGTH: 15
<212> TYPE: DNA
<213> ORGANISM: Artificial Sequence
<220> FEATURE:
<223> OTHER INFORMATION: Synthetic DNA

<400> SEQUENCE: 15
acgaaacccg cttaa                                                      15

<210> SEQ ID NO 16
<211> LENGTH: 15
<212> TYPE: DNA
<213> ORGANISM: Artificial Sequence
<220> FEATURE:
<223> OTHER INFORMATION: Synthetic DNA

<400> SEQUENCE: 16
taatccttga attag                                                      15
```

<210> SEQ ID NO 17
<211> LENGTH: 15
<212> TYPE: DNA
<213> ORGANISM: Artificial Sequence
<220> FEATURE:
<223> OTHER INFORMATION: Synthetic DNA

<400> SEQUENCE: 17
acacgtatac taatc                                                        15

<210> SEQ ID NO 18
<211> LENGTH: 15
<212> TYPE: DNA
<213> ORGANISM: Artificial Sequence
<220> FEATURE:
<223> OTHER INFORMATION: Synthetic DNA

<400> SEQUENCE: 18
catggtatgt acaac                                                        15

<210> SEQ ID NO 19
<211> LENGTH: 15
<212> TYPE: DNA
<213> ORGANISM: Artificial Sequence
<220> FEATURE:
<223> OTHER INFORMATION: Synthetic DNA

<400> SEQUENCE: 19
cattcatgag cgatc                                                        15

<210> SEQ ID NO 20
<211> LENGTH: 15
<212> TYPE: DNA
<213> ORGANISM: Artificial Sequence
<220> FEATURE:
<223> OTHER INFORMATION: Synthetic DNA

<400> SEQUENCE: 20
aaatcccata tgtag                                                        15

<210> SEQ ID NO 21
<211> LENGTH: 383
<212> TYPE: DNA
<213> ORGANISM: Artificial Sequence
<220> FEATURE:
<223> OTHER INFORMATION: Synthetic DNA

<400> SEQUENCE: 21
aaggttcttt attttaaac ttatgttaat ttattgtatc tagtagttaa tcaagagatg        60
ctctcttgga gaatttat ggtcataaaa cctatatcaa agagatgctc tcttggtata        120
ttccatactt aaaatatcta ttttggaaaa aaagtgtagc atcttcctgc ttttagtagg       180
tgtcaatcat tattaaattt cacaaaaccg tgcaagaatc ccagtttccc tatagtttgt       240
atacgttcct gatctagtat tttacttatg tttcaaatca atccaatcat gcttgtgtcc      300
gaaaattaaa aaacaagggg attggatgcc ctgtaccact attattaact tttcagaaaa       360
acgtgtagca tgtgtacata agg                                               383

<210> SEQ ID NO 22
<211> LENGTH: 383
<212> TYPE: DNA
<213> ORGANISM: Artificial Sequence
<220> FEATURE:
<223> OTHER INFORMATION: Synthetic DNA

<400> SEQUENCE: 22

```
aaggttcttt attttaaac ttatgttaat ttattgtatc tagaagttaa tcaagagatg    60
ctctcttgga gaaattttat ggtcataaaa cctatatcaa agagatgctc tcttggtata   120
ttccatactt aaaatatcta ttttggaaaa aaagtgtagc atcttcctgc ttttagtagg   180
tgtcaatcat tattaaattt cacaaaaccg tgcaagaatc ccagtttccc tatagtttgt   240
atacgttcct gatctagtat tttacttatg tttcaaatca gtccaatcat gcttgtgtcc   300
gaaaattaaa aaacaagggt attggatgcc ctgtaccact attattaact tttcagaaaa   360
acgtgtagca tgtgtacata agg                                          383
```

<210> SEQ ID NO 23
<211> LENGTH: 344
<212> TYPE: DNA
<213> ORGANISM: Artificial Sequence
<220> FEATURE:
<223> OTHER INFORMATION: Synthetic DNA

<400> SEQUENCE: 23

```
ctagaagtta atcaagagat gctctcttgg agaaattta tggtcataaa acctatatca    60 agagatgct ctcttggtat attccatact aaaatatct attttggaaa aaagtgtag    120 catcttcctg cttttagtag gtgtcaatca ttattaaatt tcacaaaacc gtgcaagaat   180
cccagtttcc ctatagtttg tatacgttcc tgatctagta ttttacttat gtttcaaatc   240
agtccaatca tgcttgtgtc cgaaaattaa aaaacaaggg tattggatgc cctgtaccac   300
tattattaac ttttcagaaa aacgtgtagc atgtgtacat aagg                   344
```

<210> SEQ ID NO 24
<211> LENGTH: 297
<212> TYPE: DNA
<213> ORGANISM: Artificial Sequence
<220> FEATURE:
<223> OTHER INFORMATION: Synthetic DNA

<400> SEQUENCE: 24

```
taatcatcca aaccctaatc tcgccaaaca accgggtact gatccaaacc ctgaaatgag    60
cacaactctt gaacctgatc acgagaatga agagcacaaa catgttatga cacatgtaaa   120
cgatggtttt tgctacatga aaaccctaga agacgaaacc cgtttaactg taaatcttga   180
aaacacattc tttgatgaaa aaccccttc gtatccggat cttatggact tttctgcatc   240
gaaaacggac gaatacgact tctatgatga acttgaagag ctgccaatgt cttcctc      297
```

<210> SEQ ID NO 25
<211> LENGTH: 297
<212> TYPE: DNA
<213> ORGANISM: Artificial Sequence
<220> FEATURE:
<223> OTHER INFORMATION: Synthetic DNA

<400> SEQUENCE: 25

```
taatcatcca aaccctaatc tcgccaaaca accgggtacc gatccaaacc ctgaaatgag    60
cacaactctt gaacctgatc acgagaatga agagcacaaa catgttatga cacatgtaaa   120
cgatggtttt tgctacatga aaaccctaga agacgaaacc cgtttaagtg taaatcttga   180
aaacacattc tttgatgaag aaccccttc gtatccggat cttatggact tttctgcatc   240
gaaaaaggac gaatacgact tctatgatga acttgaagag ttgccaatgt cttcctc      297
```

<210> SEQ ID NO 26
<211> LENGTH: 258
<212> TYPE: DNA
<213> ORGANISM: Artificial Sequence
<220> FEATURE:
<223> OTHER INFORMATION: Synthetic DNA

<400> SEQUENCE: 26

```
cgatccaaac cctgaaatga gcacaactct tgaacctgat cacgagaatg aagagcacaa      60
acatgttatg acacatgtaa acgatggttt ttgctacatg aaaccctag aagacgaaac     120 ccgtttaagt gtaaatcttg aaaacacatt ctttgatgaa gaacccctttt cgtatccgga    180 tcttatggac ttttctgcat cgaaaaagga cgaatacgac ttctatgatg aacttgaaga    240
gttgccaatg tcttcctc                                                  258
```

<210> SEQ ID NO 27
<211> LENGTH: 390
<212> TYPE: DNA
<213> ORGANISM: Artificial Sequence
<220> FEATURE:
<223> OTHER INFORMATION: Synthetic DNA

<400> SEQUENCE: 27

```
cgatggtttt tgctacatga aaaccctaga agacgaaacc cgcttaactg taaatcttga     60
aaacacattc tttgatgaaa accccttttc gtatccggat cttatggact tttctgcatc    120
gaaaacggac gaatacgact tctatgatga acttgaagag ctgccaatgt cttcctcatc    180
attcaaaagc ttcatgagaa gtaatttctt tgaggaaaga gttcttgttc aaccttattg    240
attaagaatt taagggaagc agattatata tgtaattaaa ttttggtatt tatactttga    300
acttaattaa taattataat aataatccca actagaggca cttagtggag attacttata    360
tataatacta attcaaggat tattgctggt                                     390
```

<210> SEQ ID NO 28
<211> LENGTH: 390
<212> TYPE: DNA
<213> ORGANISM: Artificial Sequence
<220> FEATURE:
<223> OTHER INFORMATION: Synthetic DNA

<400> SEQUENCE: 28

```
cgatggtttt tgctacatga aaaccctaga agacgaaacc cgcttaagtg taaatcttga     60
aaacacattc tttgatgaag aaccccttttc gtatccggat cttatggact tttctgcatc    120
gaaaaaggac gaatacgact tctatgatga acttgaagag ttgccaatgt cttcctcatc    180
attcaaaagc ttcatgagaa gtaatttctt tgaggaaaga gttcttgttc aaccttattg    240
attaagaatt taagggaagc agattatata tgtaattaaa ttttggtatt tatactttga    300
acttaattaa taattataat aataatccca actagaggca cttagtggag attacttata    360
tataatacta attcaaggat tattgctggt                                     390
```

<210> SEQ ID NO 29
<211> LENGTH: 347
<212> TYPE: DNA
<213> ORGANISM: Artificial Sequence
<220> FEATURE:
<223> OTHER INFORMATION: Synthetic DNA

<400> SEQUENCE: 29

```
ttaagtgtaa atcttgaaaa cacattcttt gatgaagaac ccctttcgta tccggatctt     60
```

```
atggactttt ctgcatcgaa aaaggacgaa tacgacttct atgatgaact tgaagagttg    120
ccaatgtctt cctcatcatt caaaagcttc atgagaagta atttctttga ggaaagagtt    180
cttgttcaac cttattgatt aagaatttaa gggaagcaga ttatatatgt aattaaattt    240
tggtatttat actttgaact taattaataa ttataataat aatcccaact agaggcactt    300
agtggagatt acttatatat aatactaatt caaggattat tgctggt                  347
```

<210> SEQ ID NO 30
<211> LENGTH: 140
<212> TYPE: DNA
<213> ORGANISM: Artificial Sequence
<220> FEATURE:
<223> OTHER INFORMATION: Synthetic DNA

<400> SEQUENCE: 30

```
cgcaaacacg tatactaatc acgtaacata ttttttattt ctaaattaaa atttgaatta     60
aagataacat aatatttatt tttagagtgt aacttctaaa aaatatcaac ctacgaaaaa    120
gttgtacata ccatgctaaa                                                140
```

<210> SEQ ID NO 31
<211> LENGTH: 288
<212> TYPE: DNA
<213> ORGANISM: Artificial Sequence
<220> FEATURE:
<223> OTHER INFORMATION: Synthetic DNA

<400> SEQUENCE: 31

```
atacaaaaac acaacccata tggtcaaatc aacccattca tgagcgatca ggtcaaattc     60
gctatctgag ctgatgcatt caactatttg gtctcttttt aacatttatt ttttttatta    120
ttttgaatgt agaaactttg gaactactca actggtaagt tcttgaagat gtataccggt    180
catgtaaaca aaacatattg tataactccg acttttctg taacaaatgg aaaatatatt     240
gttagtggtt cagaagatca ttgtgtctac atatgggatt tacaaggg                 288
```

<210> SEQ ID NO 32
<211> LENGTH: 288
<212> TYPE: DNA
<213> ORGANISM: Artificial Sequence
<220> FEATURE:
<223> OTHER INFORMATION: Synthetic DNA

<400> SEQUENCE: 32

```
atacaaaaac acaacccata tggtcaaatc aacccattca tgagcgatcg ggtcaaattc     60
gctatctgag ctgatgcatt caactatttg gtctcttttt aacatttatt ttttttatta    120
ttttgaatgt agaaactttg gaactactca actggtaagt tcttgaagat gtataccggt    180
catgtaaaca aaacatattg tataactccg acttttctg taacaaatgg aaaatatatt     240
gttagtggtt cagaagatca ttgtgtctac atatgggatt tacaaggg                 288
```

<210> SEQ ID NO 33
<211> LENGTH: 240
<212> TYPE: DNA
<213> ORGANISM: Artificial Sequence
<220> FEATURE:
<223> OTHER INFORMATION: Synthetic DNA

<400> SEQUENCE: 33

```
cgggtcaaat tcgctatctg agctgatgca ttcaactatt tggtctcttt ttaacattta     60
```

| | |
|---|---|
| ttttttttat tattttgaat gtagaaactt tggaactact caactggtaa gttcttgaag | 120 |
| atgtataccg gtcatgtaaa caaaacatat tgtataactc cgactttttc tgtaacaaat | 180 |
| ggaaaatata ttgttagtgg ttcagaagat cattgtgtct acatatggga tttacaaggg | 240 |

<210> SEQ ID NO 34
<211> LENGTH: 158
<212> TYPE: DNA
<213> ORGANISM: Artificial Sequence
<220> FEATURE:
<223> OTHER INFORMATION: Synthetic DNA

<400> SEQUENCE: 34

| | |
|---|---|
| cgcaaacacg tatactaatc acgtaacata ttttttattt ctaaattaaa attttataac | 60 |
| aatatcatac ttgaattaaa gataacataa tatttatttt tagagtgtaa cttctaaaaa | 120 |
| atatcaacct acgaaaaagt tgtacatacc atgctaaa | 158 |

<210> SEQ ID NO 35
<211> LENGTH: 141
<212> TYPE: DNA
<213> ORGANISM: Artificial Sequence
<220> FEATURE:
<223> OTHER INFORMATION: Synthetic DNA

<400> SEQUENCE: 35

| | |
|---|---|
| aaggttcttt attttaaac ttatgttaat ttattgtatc ttgtagttaa tcaagagatg | 60 |
| ctctcttgga gaaattttat ggtcataaaa cctatatcaa agagatgctc tcttggtata | 120 |
| ttccatactt aaaatatcta t | 141 |

<210> SEQ ID NO 36
<211> LENGTH: 141
<212> TYPE: DNA
<213> ORGANISM: Artificial Sequence
<220> FEATURE:
<223> OTHER INFORMATION: Synthetic DNA

<400> SEQUENCE: 36

| | |
|---|---|
| aaggttcttt attttaaac ttatgttaat ttattgtatc ttgaagttaa tcaagagatg | 60 |
| ctctcttgga gaaattttat ggtcataaaa cctatatcaa agagatgctc tcttggtata | 120 |
| ttccatactt aaaatatcta t | 141 |

<210> SEQ ID NO 37
<211> LENGTH: 137
<212> TYPE: DNA
<213> ORGANISM: Artificial Sequence
<220> FEATURE:
<223> OTHER INFORMATION: Synthetic DNA

<400> SEQUENCE: 37

| | |
|---|---|
| taatcatcca accctaatc tcgccaaaca accgaatact gatccaaacc ctgaaatgag | 60 |
| cacaactctt gaacctgatc acgagaatga agagcacaaa catgttatga cacatgtaaa | 120 |
| cgatggtttt tgctaca | 137 |

<210> SEQ ID NO 38
<211> LENGTH: 137
<212> TYPE: DNA
<213> ORGANISM: Artificial Sequence
<220> FEATURE:
<223> OTHER INFORMATION: Synthetic DNA

<400> SEQUENCE: 38

```
taatcatcca aaccctaatc tcgccaaaca accgaatacc gatccaaacc ctgaaatgag    60
cacaactctt gaacctgatc acgagaatga agagcacaaa catgttatga cacatgtaaa   120
cgatggtttt tgctaca                                                  137
```

<210> SEQ ID NO 39
<211> LENGTH: 137
<212> TYPE: DNA
<213> ORGANISM: Artificial Sequence
<220> FEATURE:
<223> OTHER INFORMATION: Synthetic DNA

<400> SEQUENCE: 39

```
cgatggtttt tgctacatga aaccctaga agacgaaacc cgtttaactg taaatcttga    60
aaacacattc tttgatgaag aacccctttc gtatccggat cttatggact tttctgcatc   120
gaaaaaggac gaatacg                                                  137
```

<210> SEQ ID NO 40
<211> LENGTH: 137
<212> TYPE: DNA
<213> ORGANISM: Artificial Sequence
<220> FEATURE:
<223> OTHER INFORMATION: Synthetic DNA

<400> SEQUENCE: 40

```
cgatggtttt tgctacatga aaccctaga agacgaaacc cgtttaagtg taaatcttga    60
aaacacattc tttgatgaag aacccctttc gtatccggat cttatggact tttctgcatc   120
gaaaaaggac gaatacg                                                  137
```

<210> SEQ ID NO 41
<211> LENGTH: 140
<212> TYPE: DNA
<213> ORGANISM: Artificial Sequence
<220> FEATURE:
<223> OTHER INFORMATION: Synthetic DNA

<400> SEQUENCE: 41

```
cgcaaacacg tatactaatc acgtaacata ttttttattt ctaaattaaa atttgaatta    60
aagataacat aatatttatt tttagagtgt aacttctaaa aaatatcaac ctacgaaaaa   120
gttgtacata ccatgctaaa                                               140
```

<210> SEQ ID NO 42
<211> LENGTH: 158
<212> TYPE: DNA
<213> ORGANISM: Artificial Sequence
<220> FEATURE:
<223> OTHER INFORMATION: Synthetic DNA

<400> SEQUENCE: 42

```
cgcaaacacg tatactaatc acgtaacata ttttttattt ctaaattaaa attttataac    60
aatatcatac ttgaattaaa gataacataa tatttatttt tagagtgtaa cttctaaaaa   120
atatcaacct acgaaaaagt tgtacatacc atgctaaa                           158
```

<210> SEQ ID NO 43
<211> LENGTH: 139
<212> TYPE: DNA
<213> ORGANISM: Artificial Sequence
<220> FEATURE:
<223> OTHER INFORMATION: Synthetic DNA

<400> SEQUENCE: 43
atacaaaaac acaacccata tggtcaaatc aacccattca tgagtaatca ggtcaaattc    60
gctatctgag ctgatgcatt caactatttg gtctcttttt aacatttatt tttttatta   120 ttttgaatgt agaaacttt                                                139

<210> SEQ ID NO 44
<211> LENGTH: 139
<212> TYPE: DNA
<213> ORGANISM: Artificial Sequence
<220> FEATURE:
<223> OTHER INFORMATION: Synthetic DNA

<400> SEQUENCE: 44
atacaaaaac acaacccata tggtcaaatc aacccattca tgagtaatcg ggtcaaattc    60
gctatctgag ctgatgcatt caactatttg gtctcttttt aacatttatt tttttatta   120 ttttgaatgt agaaacttt                                                139

<210> SEQ ID NO 45
<211> LENGTH: 15
<212> TYPE: DNA
<213> ORGANISM: Artificial Sequence
<220> FEATURE:
<223> OTHER INFORMATION: Synthetic DNA

<400> SEQUENCE: 45
aaggttcttt atttt                                                     15

<210> SEQ ID NO 46
<211> LENGTH: 15
<212> TYPE: DNA
<213> ORGANISM: Artificial Sequence
<220> FEATURE:
<223> OTHER INFORMATION: Synthetic DNA

<400> SEQUENCE: 46
atagatattt taagt                                                     15

<210> SEQ ID NO 47
<211> LENGTH: 15
<212> TYPE: DNA
<213> ORGANISM: Artificial Sequence
<220> FEATURE:
<223> OTHER INFORMATION: Synthetic DNA

<400> SEQUENCE: 47
taatcatcca aaccc                                                     15

<210> SEQ ID NO 48
<211> LENGTH: 15
<212> TYPE: DNA
<213> ORGANISM: Artificial Sequence
<220> FEATURE:
<223> OTHER INFORMATION: Synthetic DNA

<400> SEQUENCE: 48
tgtagcaaaa accat                                                     15

<210> SEQ ID NO 49
<211> LENGTH: 15
<212> TYPE: DNA
<213> ORGANISM: Artificial Sequence
<220> FEATURE:
<223> OTHER INFORMATION: Synthetic DNA

<400> SEQUENCE: 49
cgatggtttt tgcta                                               15

<210> SEQ ID NO 50
<211> LENGTH: 15
<212> TYPE: DNA
<213> ORGANISM: Artificial Sequence
<220> FEATURE:
<223> OTHER INFORMATION: Synthetic DNA

<400> SEQUENCE: 50
cgtattcgtc cttttt                                              15

<210> SEQ ID NO 51
<211> LENGTH: 15
<212> TYPE: DNA
<213> ORGANISM: Artificial Sequence
<220> FEATURE:
<223> OTHER INFORMATION: Synthetic DNA

<400> SEQUENCE: 51
cgcaaacacg tatac                                               15

<210> SEQ ID NO 52
<211> LENGTH: 15
<212> TYPE: DNA
<213> ORGANISM: Artificial Sequence
<220> FEATURE:
<223> OTHER INFORMATION: Synthetic DNA

<400> SEQUENCE: 52
tttagcatgg tatgt                                               15

<210> SEQ ID NO 53
<211> LENGTH: 15
<212> TYPE: DNA
<213> ORGANISM: Artificial Sequence
<220> FEATURE:
<223> OTHER INFORMATION: Synthetic DNA

<400> SEQUENCE: 53
atacaaaaac acaac                                               15

<210> SEQ ID NO 54
<211> LENGTH: 15
<212> TYPE: DNA
<213> ORGANISM: Artificial Sequence
<220> FEATURE:
<223> OTHER INFORMATION: Synthetic DNA

<400> SEQUENCE: 54
aaagtttcta cattc                                               15

<210> SEQ ID NO 55
<211> LENGTH: 21
<212> TYPE: DNA
<213> ORGANISM: Artificial Sequence
<220> FEATURE:
<223> OTHER INFORMATION: Synthetic DNA

<400> SEQUENCE: 55
ttgtatcttg tagttaatca a                                        21

<210> SEQ ID NO 56

```
<211> LENGTH: 21
<212> TYPE: DNA
<213> ORGANISM: Artificial Sequence
<220> FEATURE:
<223> OTHER INFORMATION: Synthetic DNA

<400> SEQUENCE: 56
ttgtatcttg aagttaatca a                                              21

<210> SEQ ID NO 57
<211> LENGTH: 21
<212> TYPE: DNA
<213> ORGANISM: Artificial Sequence
<220> FEATURE:
<223> OTHER INFORMATION: Synthetic DNA

<400> SEQUENCE: 57
aaccgaatac tgatccaaac c                                              21

<210> SEQ ID NO 58
<211> LENGTH: 21
<212> TYPE: DNA
<213> ORGANISM: Artificial Sequence
<220> FEATURE:
<223> OTHER INFORMATION: Synthetic DNA

<400> SEQUENCE: 58
aaccgaatac cgatccaaac c                                              21

<210> SEQ ID NO 59
<211> LENGTH: 21
<212> TYPE: DNA
<213> ORGANISM: Artificial Sequence
<220> FEATURE:
<223> OTHER INFORMATION: Synthetic DNA

<400> SEQUENCE: 59
acccgtttaa ctgtaaatct t                                              21

<210> SEQ ID NO 60
<211> LENGTH: 21
<212> TYPE: DNA
<213> ORGANISM: Artificial Sequence
<220> FEATURE:
<223> OTHER INFORMATION: Synthetic DNA

<400> SEQUENCE: 60
acccgtttaa gtgtaaatct t                                              21

<210> SEQ ID NO 61
<211> LENGTH: 20
<212> TYPE: DNA
<213> ORGANISM: Artificial Sequence
<220> FEATURE:
<223> OTHER INFORMATION: Synthetic DNA

<400> SEQUENCE: 61
attaaaattt gaattaaaga                                                20

<210> SEQ ID NO 62
<211> LENGTH: 38
<212> TYPE: DNA
<213> ORGANISM: Artificial Sequence
<220> FEATURE:
<223> OTHER INFORMATION: Synthetic DNA

<400> SEQUENCE: 62
```
attaaaattt tataacaata tcatacttga attaaaga                        38

<210> SEQ ID NO 63
<211> LENGTH: 21
<212> TYPE: DNA
<213> ORGANISM: Artificial Sequence
<220> FEATURE:
<223> OTHER INFORMATION: Synthetic DNA

<400> SEQUENCE: 63
atgagtaatc aggtcaaatt c                                         21

<210> SEQ ID NO 64
<211> LENGTH: 21
<212> TYPE: DNA
<213> ORGANISM: Artificial Sequence
<220> FEATURE:
<223> OTHER INFORMATION: Synthetic DNA

<400> SEQUENCE: 64
atgagtaatc gggtcaaatt c                                         21

<210> SEQ ID NO 65
<211> LENGTH: 41
<212> TYPE: DNA
<213> ORGANISM: Artificial Sequence
<220> FEATURE:
<223> OTHER INFORMATION: Synthetic DNA

<400> SEQUENCE: 65
tgttaattta ttgtatcttg tagttaatca agagatgctc t                   41

<210> SEQ ID NO 66
<211> LENGTH: 41
<212> TYPE: DNA
<213> ORGANISM: Artificial Sequence
<220> FEATURE:
<223> OTHER INFORMATION: Synthetic DNA

<400> SEQUENCE: 66
tgttaattta ttgtatcttg aagttaatca agagatgctc t                   41

<210> SEQ ID NO 67
<211> LENGTH: 41
<212> TYPE: DNA
<213> ORGANISM: Artificial Sequence
<220> FEATURE:
<223> OTHER INFORMATION: Synthetic DNA

<400> SEQUENCE: 67
ctcgccaaac aaccgaatac tgatccaaac cctgaaatga g                   41

<210> SEQ ID NO 68
<211> LENGTH: 41
<212> TYPE: DNA
<213> ORGANISM: Artificial Sequence
<220> FEATURE:
<223> OTHER INFORMATION: Synthetic DNA

<400> SEQUENCE: 68
ctcgccaaac aaccgaatac cgatccaaac cctgaaatga g                   41

<210> SEQ ID NO 69
<211> LENGTH: 41
<212> TYPE: DNA

<213> ORGANISM: Artificial Sequence
<220> FEATURE:
<223> OTHER INFORMATION: Synthetic DNA

<400> SEQUENCE: 69
agaagacgaa acccgtttaa ctgtaaatct tgaaaacaca t                41

<210> SEQ ID NO 70
<211> LENGTH: 41
<212> TYPE: DNA
<213> ORGANISM: Artificial Sequence
<220> FEATURE:
<223> OTHER INFORMATION: Synthetic DNA

<400> SEQUENCE: 70
agaagacgaa acccgtttaa gtgtaaatct tgaaaacaca t                41

<210> SEQ ID NO 71
<211> LENGTH: 40
<212> TYPE: DNA
<213> ORGANISM: Artificial Sequence
<220> FEATURE:
<223> OTHER INFORMATION: Synthetic DNA

<400> SEQUENCE: 71
ttatttctaa attaaaattt gaattaaaga taacataata                  40

<210> SEQ ID NO 72
<211> LENGTH: 58
<212> TYPE: DNA
<213> ORGANISM: Artificial Sequence
<220> FEATURE:
<223> OTHER INFORMATION: Synthetic DNA

<400> SEQUENCE: 72
ttatttctaa attaaaattt tataacaata tcatacttga attaaagata acataata      58

<210> SEQ ID NO 73
<211> LENGTH: 41
<212> TYPE: DNA
<213> ORGANISM: Artificial Sequence
<220> FEATURE:
<223> OTHER INFORMATION: Synthetic DNA

<400> SEQUENCE: 73
caacccattc atgagtaatc aggtcaaatt cgctatctga g                41

<210> SEQ ID NO 74
<211> LENGTH: 41
<212> TYPE: DNA
<213> ORGANISM: Artificial Sequence
<220> FEATURE:
<223> OTHER INFORMATION: Synthetic DNA

<400> SEQUENCE: 74
caacccattc atgagtaatc gggtcaaatt cgctatctga g                41

<210> SEQ ID NO 75
<211> LENGTH: 61
<212> TYPE: DNA
<213> ORGANISM: Artificial Sequence
<220> FEATURE:
<223> OTHER INFORMATION: Synthetic DNA

<400> SEQUENCE: 75
tttaaactta tgttaattta ttgtatcttg tagttaatca agagatgctc tcttggagaa    60
a                                                                61

<210> SEQ ID NO 76
<211> LENGTH: 61
<212> TYPE: DNA
<213> ORGANISM: Artificial Sequence
<220> FEATURE:
<223> OTHER INFORMATION: Synthetic DNA

<400> SEQUENCE: 76
tttaaactta tgttaatttta ttgtatcttg aagttaatca agagatgctc tcttggagaa    60
a                                                                61

<210> SEQ ID NO 77
<211> LENGTH: 61
<212> TYPE: DNA
<213> ORGANISM: Artificial Sequence
<220> FEATURE:
<223> OTHER INFORMATION: Synthetic DNA

<400> SEQUENCE: 77
aaaccctaat ctcgccaaac aaccgaatac tgatccaaac cctgaaatga gcacaactct    60
t                                                                61

<210> SEQ ID NO 78
<211> LENGTH: 61
<212> TYPE: DNA
<213> ORGANISM: Artificial Sequence
<220> FEATURE:
<223> OTHER INFORMATION: Synthetic DNA

<400> SEQUENCE: 78
aaaccctaat ctcgccaaac aaccgaatac cgatccaaac cctgaaatga gcacaactct    60
t                                                                61

<210> SEQ ID NO 79
<211> LENGTH: 61
<212> TYPE: DNA
<213> ORGANISM: Artificial Sequence
<220> FEATURE:
<223> OTHER INFORMATION: Synthetic DNA

<400> SEQUENCE: 79
tgaaaaccct agaagacgaa acccgtttaa ctgtaaatct tgaaaacaca ttctttgatg    60
a                                                                61

<210> SEQ ID NO 80
<211> LENGTH: 61
<212> TYPE: DNA
<213> ORGANISM: Artificial Sequence
<220> FEATURE:
<223> OTHER INFORMATION: Synthetic DNA

<400> SEQUENCE: 80
tgaaaaccct agaagacgaa acccgtttaa gtgtaaatct tgaaaacaca ttctttgatg    60
a                                                                61

<210> SEQ ID NO 81
<211> LENGTH: 60
<212> TYPE: DNA
<213> ORGANISM: Artificial Sequence
<220> FEATURE:

```
<223> OTHER INFORMATION: Synthetic DNA

<400> SEQUENCE: 81
aacatatttt ttatttctaa attaaaattt gaattaaaga taacataata tttattttta        60

<210> SEQ ID NO 82
<211> LENGTH: 78
<212> TYPE: DNA
<213> ORGANISM: Artificial Sequence
<220> FEATURE:
<223> OTHER INFORMATION: Synthetic DNA

<400> SEQUENCE: 82
aacatatttt ttatttctaa attaaaattt tataacaata tcatacttga attaaagata        60
acataatatt tattttta                                                     78

<210> SEQ ID NO 83
<211> LENGTH: 61
<212> TYPE: DNA
<213> ORGANISM: Artificial Sequence
<220> FEATURE:
<223> OTHER INFORMATION: Synthetic DNA

<400> SEQUENCE: 83
atggtcaaat caacccattc atgagtaatc aggtcaaatt cgctatctga gctgatgcat        60
t                                                                       61

<210> SEQ ID NO 84
<211> LENGTH: 61
<212> TYPE: DNA
<213> ORGANISM: Artificial Sequence
<220> FEATURE:
<223> OTHER INFORMATION: Synthetic DNA

<400> SEQUENCE: 84
atggtcaaat caacccattc atgagtaatc gggtcaaatt cgctatctga gctgatgcat        60
t                                                                       61
```